US008609810B2

(12) United States Patent
Nawroth et al.

(10) Patent No.: US 8,609,810 B2
(45) Date of Patent: Dec. 17, 2013

(54) METHYLGLYOXAL-SCAVENGING COMPOUNDS AND THEIR USE FOR THE PREVENTION AND TREATMENT OF PAIN AND/OR HYPERALGESIA

(75) Inventors: Peter Nawroth, Leimen (DE); Angelika Bierhaus, Heidelberg (DE); Thomas Fleming, Heidelberg (DE)

(73) Assignee: Ruprecht-Karls-Universitat Heidelberg, Heidelberg (DE)

( * ) Notice: Subject to any disclaimer, the term of this patent is extended or adjusted under 35 U.S.C. 154(b) by 0 days.

(21) Appl. No.: 13/319,473

(22) PCT Filed: May 26, 2010

(86) PCT No.: PCT/EP2010/003186
§ 371 (c)(1),
(2), (4) Date: Jan. 19, 2012

(87) PCT Pub. No.: WO2010/136182
PCT Pub. Date: Dec. 2, 2010

(65) Prior Publication Data

US 2012/0115789 A1 May 10, 2012

Related U.S. Application Data

(60) Provisional application No. 61/182,203, filed on May 29, 2009.

(51) Int. Cl.
*A61K 38/00* (2006.01)

(52) U.S. Cl.
USPC .......... 530/324; 514/1.1; 514/17.7; 514/17.8; 514/18.3

(58) Field of Classification Search
None
See application file for complete search history.

(56) References Cited

PUBLICATIONS

Dobler, et al., "Increased Dicarbonyl Metabolism in Endothelial Cells in Hyperglycemia Induces Anoikis and Impairs Angiogenesis by RGD and GFOGER Motif Modification" *Diabetes*, 2006, pp. 1961-1969, vol. 55, No. 7.

Ward, R.A. and McLeish, K.R., "Methylglyoxal: A Stimulus to Neutrophil Oxygen Radical Production in Chronic Renal Failure?" *Nephrol Dial Transplant*, 2004, pp. 1702-1707, vol. 19, No. 7.

*Primary Examiner* — John Ulm
(74) *Attorney, Agent, or Firm* — Saliwanchik, Lloyd & Eisenschenk

(57) ABSTRACT

The present invention relates to compounds which inhibit or antagonize the binding of methylglyoxal (MG) and/or other reactive carbonyl species (RCS) to an arginine- or lysine-containing protein, preferably an arginine- or lysine-containing cellular protein, such as a sodium ion channel, e.g. the sodium ion channel Na(v)1.8. Preferred scavenger compounds are peptides comprising several or multiple repeats of the amino acid sequence motif Gly-Glu-X-Pro (GEXP), wherein X is Arg or Lys, and pharmaceutical compositions thereof. The present invention furthermore relates to the use of the compounds as scavenger or antagonists of methylglyoxal and/or related reactive carbonyl species (RCS). The present invention furthermore relates to the use of the compounds for the prevention and/or treatment of pain, hyperalgesia and pain related diseases, in particular pain and/or hyperalgesia caused by or associated with methylglyoxal and/or reactive carbonyl species (RCS).

18 Claims, 20 Drawing Sheets

$Na_v1.8$

Figure 4 A and B
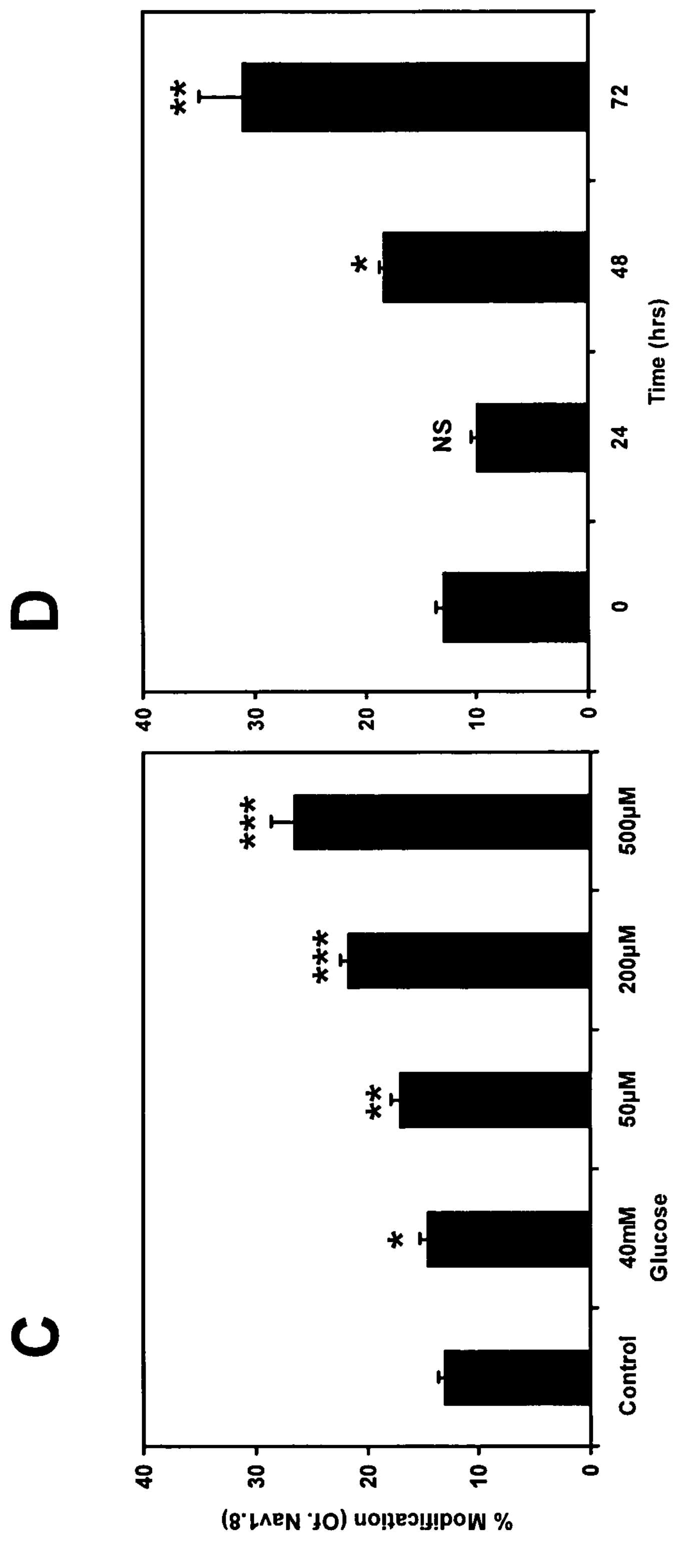

METHYLGLYOXAL-SCAVENGING COMPOUNDS AND THEIR USE FOR THE PREVENTION AND TREATMENT OF PAIN AND/OR HYPERALGESIA

CROSS REFERENCE TO A RELATED APPLICATION

This application is a National Stage Application of International Application Number PCT/EP2010/003186, filed May 26, 2010; which claims the benefit of U.S. Provisional Application Ser. No. 61/182,203, filed May 29, 2009; which are incorporated herein by reference in their entirety.

The present invention relates to compounds which inhibit or antagonize the binding of methylglyoxal (MG) and/or other reactive carbonyl species (RCS) to an arginine- or lysine-containing protein, preferably an arginine- or lysine-containing cellular protein, such as a sodium ion channel, e.g. the sodium ion channel Na(v)1.8. Preferred scavenger compounds are peptides comprising several or multiple repeats of the amino acid sequence motif Gly-Glu-X-Pro (GEXP) (SEQ ID NO: 1), wherein X is Arg or Lys, and pharmaceutical compositions thereof. The present invention furthermore relates to the use of the compounds as scavenger or antagonists of methylglyoxal and/or related reactive carbonyl species (RCS). The present invention furthermore relates to the use of the compounds for the prevention and/or treatment of pain, hyperalgesia and pain related diseases, in particular pain and/or hyperalgesia caused by or associated with methylglyoxal and/or reactive carbonyl species (RCS).

BACKGROUND OF THE INVENTION

Methylglyoxal (MG), also called pyruvaldehyde or 2-oxopropanal ($CH_3$—CO—CH═O) is the aldehyde form of pyruvic acid. It has two carbonyl groups, so it is a dicarbonyl compound. In organisms, methylglyoxal is formed as a side-product of several metabolic pathways. MG may be generated from 3-amino acetone, which is an intermediate of threonine catabolism, as well as through lipid peroxidation. However, the most important source is glycolysis, where methylglyoxal arises from non enzymatic phosphate elimination from glyceraldehyde phosphate and dihydroxyacetone phosphate, two intermediates of glycolysis. Since methylglyoxal is highly cytotoxic the body developed several detoxification mechanisms. One of these is the glyoxylase system. Methylglyoxal reacts with glutathione forming a hemithioacetal. This is converted into S-D-lactoyl-glutathione by glyoxylase I (GLO-I), and then further metabolised into D-lactate by glyoxylase II (GLO-II).

Why methylglyoxal is produced remains unknown, but several articles indicate that methylglyoxal is involved in the formation of advanced glycation endproducts (AGEs). In fact, methylglyoxal is proven to be the most important glycation agent (forming AGEs). In this process, methylglyoxal reacts with free amino groups of lysine and arginine residues of proteins forming AGEs (see FIG. 1). Other glycation agents include reducing sugars like glucose, galactose, allose and ribose.

Formation of methylglyoxal and related reactive carbonyl species (RCS) is closely linked to the rate of glycolysis and the presence of glycolytic intermediates. Hence, in conditions where there is increased glycolytic flux and an increased dependence on glycolysis for energy, the rate of methylglyoxal and RCS formation will also be increased. This has been shown to be the case in patients with diabetes mellitus, where complications such as nephropathy, neuropathy and retinopathy have been linked to increases in cellular levels of advanced glycation endproducts (AGEs). While diabetes has been the main area of research, new evidence is now emerging of the pivot role that RCS, in particularly methylglyoxal, plays in the progression and severity of various diseases. (see Table 1)

TABLE 1

| Disease | Selected Refs |
|---|---|
| Alzheimer's Disease | 1-11 |
| Amyotrophic lateral sclerosis | 12, 13 |
| Cataractogenesis | 14, 15, 16 |
| Chronic renal failure and chronic or acute Uraemia | 17-25 |
| Cystic fibrosis | 26, 27 |
| Dementia with Lewy bodies | 28 |
| Diabetes and its complications | 38 |
| Ischaemia-reperfusion | 29 |
| Pre-eclampsia | 30 |
| Psoriasis | 31 |
| Rheumatoid arthritis and juvenile chronic arthritis | 32, 33 |
| Severe sepsis | 34, 35 |
| Systemic amyloidosis | 36 |
| Parkinson's Disease | 37 |
| Painful bowel disease | |

Sodium ion channels are integral membrane proteins that form ion channels, conducting sodium ions through the cell plasma membrane. They are classified according to the trigger that opens the channel for such ions, i.e. either a voltage-change (voltage-gated sodium channels) or binding of a substance (a ligand) to the channel (ligand-gated sodium channels). In excitable cells such as neurons, myocytes, and certain types of glia, sodium channels are responsible for the rising phase of action potentials. Sodium channels can often be isolated from cells as a complex of two types of protein subunits, α and β. An α-subunit forms the core of the channel. When the α-subunit protein is expressed by a cell, it is able to form channels which conduct $Na^+$ in a voltage-gated way, even if β-subunits are not expressed. When β-subunits assemble with α-subunits the resulting complex can display altered voltage dependence and cellular localization. The α-subunit has four repeat domains, labeled I through IV, each containing six membrane-spanning regions, labeled S1 through S6. The highly conserved S4 region acts as the channel's voltage sensor. The voltage sensitivity of the channel is due to positive amino acids located at every third position. When stimulated by a change in transmembrane voltage, this region moves toward the extracellular side of the cell membrane, allowing the channel to become permeable to ions. The ions are conducted through a pore, which can be broken into two regions. The more external (extracellular) portion of the pore is formed by the "P-loops" (the region between S5 and S6) of the four domains. This region is the most narrow part of the pore and is responsible for its ion selectivity. The inner portion (cytoplasmic) of the pore is formed by the combined S5 and S6 regions of the four domains. See e.g. FIG. 2B.

Voltage-gated sodium channels have three types of states: deactivated (closed), activated (open), and inactivated (closed). Channels in the deactivated state are thought to be blocked on their intracellular side by an "activation gate", which is removed in response to stimulation that opens the channel. The ability to inactivate due to a tethered plug (formed by domains III and IV of the alpha subunit), called an inactivation gate, that blocks the inside of the channel shortly after it has been activated. During an action potential the channel remains inactivated for a few milliseconds after depolarization. The inactivation is removed when the membrane potential of the cell repolarizes following the falling phase of the action potential. This allows the channels to be activated again during the next action potential.

There are a number of chemicals and genetic disorders which disrupt normal functioning of sodium channels and have disastrous consequences for the organism. Chemicals which can block sodium channels include Tetrodotoxin (produced by the puffer fish), Saxitoxin (produced by a dinoflagellate), Conotoxin (produced by cone snails), as well as the synthetic, local anesthetics, Lidocaine and Novocaine. Genetic disorders which effect the functioning of sodium channels, including Skaker (Sh) gene, human hyperkalaemic periodic paralysis (HyerPP), Episodic ataxia (EA), and Brugada syndrome.

In diabetes mellitus, neuropathy, which is one of three main major complications associated with the diseases, is frequently observed with patients exhibiting one or more types of stimulus-evolved pain, including increased responsiveness to noxious stimuli (hyperalgesia) as well as hyper-responsiveness to normally innocuous stimuli (allodynia). The underlying mechanism of persistent pain diabetic patients remains poorly understood and as such there are little or no effective therapeutic treatments which can either delay or prevent the onset of symptoms.

The present invention aims to provide means and methods for scavenging and/or antagonizing methylglyoxal and/or reactive carbonyl species (RCS), which allow an improved prevention and/or treatment of pain, in particular pain and/or hyperalgesia caused by or associated with methylglyoxal and/or reactive carbonyl species (RCS).

SUMMARY OF THE INVENTION

According to the present invention this object is solved by providing a compound which inhibits or antagonizes the binding of methylglyoxal (MG) and/or reactive carbonyl species (RCS) to an arginine- or lysine-containing protein.

The arginine- or lysine-containing protein is preferably an arginine- or lysine-containing cellular protein, such as a sodium ion channel, e.g. the sodium ion channel Na(v)1.8.

A preferred compound is a peptide comprising several and/or multiple repeats of a GEXP motif.

The GEXP motif of the peptides of the present invention is $$[\text{Gly-Glu-X-Pro (SEQ ID NO: 1)}]_n$$

wherein

X is arginine (Arg) or lysine (Lys),

N, the total number of GEXP repeats, is at least 2 and is preferably in the range $2 \leq n \leq 100$.

According to the present invention this object is furthermore solved by providing the compounds of the present invention for use in medicine.

According to the present invention this object is furthermore solved by providing the compounds of the present invention as scavenger of methylglyoxal and/or reactive carbonyl species (RCS).

According to the present invention this object is furthermore solved by providing the compounds of the present invention as antagonist of methylglyoxal for binding to an arginine- or lysine-containing protein, preferably an arginine- or lysine-containing cellular protein, such as a sodium ion channel, e.g. the sodium ion channel Na(v)1.8.

According to the present invention this object is furthermore solved by providing the compounds of the present invention for the prevention and/or treatment of pain and/or hyperalgesia, in particular pain and/or hyperalgesia caused by or associated with methylglyoxal and/or reactive carbonyl species (RCS).

According to the present invention this object is furthermore solved by providing pharmaceutical compositions comprising at least one compound of the present invention and optionally a pharmaceutically acceptable carrier and/or excipient.

According to the present invention this object is furthermore solved by a method for identifying/screening compounds that influence pain and/or hyperalgesia, in particular pain and/or hyperalgesia caused by or associated with methylglyoxal and/or reactive carbonyl Species (RCS).

Said Method Comprises (a) providing a compound to be screened, (b) providing a compound according to the present invention, (c) determining the effect of the compound to be screened of (a) on the development and/or progression of pain and/or hyperalgesia.

According to the present invention this object is furthermore solved by providing compounds identified in the screening method of the invention.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Methylglyoxal-Scavenging Compounds

As outlined above, the present invention provides compounds which inhibit or antagonize the binding of methylglyoxal (MG) and/or reactive carbonyl species (RCS) to an arginine- or lysine-containing protein, i.e. the binding of methylglyoxal (MG) and/or reactive carbonyl species (RCS) to arginine or lysine residues of these proteins.

An arginine- or lysine-containing protein is preferably an arginine- or lysine-containing cellular protein, more preferably an arginine-containing cellular protein, such as a sodium ion channel, e.g. the sodium ion channel Na(v)1.8.

A compound according to the present invention is capable to bind and scavenge methylglyoxal and other RCS in vivo and in vitro, and/or antagonize and/or compete with methylglyoxal and other RCS for binding to proteins, preferably arginine- or lysine-containing (cellular) proteins, such as the sodium ion channel Na(v)1.8, and/or prevent the modification of proteins, preferably arginine- or lysine-containing (cellular) proteins, such as the sodium ion channel Na(v)1.8, by methylglyoxal and other RCS, and/or inhibit and/or prevent the formation of advanced glycation endproducts (AGEs) by methylglyoxal and other RCS.

The "scavenging potential" of a compound as used herein can be viewed as the amount of methylglyoxal which can react with a compound of the invention and therefore be the effective amount of methylglyoxal or similarly acting reactive metabolites (such as reactive carbonyl species (RCS)) which are removed from binding to arginine- or lysine-containing (cellular) proteins at any situation in which methylglyoxal or similarly acting reactive metabolites (such as reactive carbonyl species (RCS)) are elevated.

The inventors have found a modification by methylglyoxal of voltage-gated sodium channel 1.8 ($Na_v1.8$; Scn10a), which is a TTX-resistant channel expressed exclusively in the dorsal root ganglia and presented here as an example of other similarly acting channels. Thus, the function of sodium channel $Na_v1.8$ and the other channels can be modulated by methylglyoxal or similarly acting reactive metabolites (such as reactive carbonyl species (RCS)). This finding of the inventors provides, for example, a novel mechanism for the development and progression of diabetic neuropathy.

The inventors have furthermore found that compounds, which inhibit or antagonize the binding of methylglyoxal (MG) and/or reactive carbonyl species (RCS) to an arginine (or lysine)-containing protein, preferably an arginine (or lysine)-containing cellular protein, such as a sodium ion channel, e.g. the sodium ion channel Na(v)1.8 (i.e. the methylglyoxal-scavenging compounds of the present invention), are suitable for a novel and specific treatment/therapy for pain and/or hyperalgesia, wherein the components causing the pain/hyperalgesia or are associated therewith (namely methylglyoxal (MG) and/or reactive carbonyl species (RCS)) are targeted. See further below for more details.

GEXP Peptides/Peptides Comprising Repeated GEXP Motifs

A preferred embodiment of the scavenging compounds of the present invention are peptides comprising several and/or multiple repeats of a GEXP motif.

The GEXP motif of the peptides of the present invention is.

$$[\text{Gly-Glu-X-Pro}]_n.$$

X is a basic amino acid residue, preferably arginine (Arg) or lysine (Lys). See also SEQ ID NO. 1.

The GEXP motif is a tetra-peptide of glycine (Gly), glutamate (Glu), X (wherein X is arginine (Arg) or lysine (Lys) and proline (Pro). This motif is itself based upon the structure of collagen.

The extracellular matrix (ECM), of which collagen is the most abundant component has been extensively studied in respect to post-translational modifications by methylglyoxal. It has been proposed that under conditions of hyperglycaemia and altered glucose metabolism, such as in diabetes mellitus, there is an excess generation of methylglyoxal which subsequently modifies key arginine residues in collagen, specifically the GFOGER and RGD integrin binding sites, causing endothelial cell detachment, anoikis and inhibition of angiogenesis. Collagen contains three polypeptide strands each consisting of two repeating motifs, either Gly-Pro-Y or Gly-Z-Hyp, where Y and Z may be any other amino acid residue. The high content of proline (Pro) and/or hydroxyproline (Hyp), with their geometrically constrained carboxyl and (secondary) amino groups, results in the tendency of the individual polypeptide chains to form left-handed helices spontaneously, without any intrachain hydrogen bonding. Collagen, with its simple structure and subsequent high potential for modification, therefore represents an ideal model for the construction of a synthetic peptide scavenger of methylglyoxal.

In a preferred embodiment, the GEXP motif is a GERP motif, i.e. X is Arg.

The total number of the GEXP motif (i.e. the repeat number thereof, n) is at least 2.

Preferably, the at least two GEXP motifs are adjacent/contiguous to each other. Preferably, the total number of GEXP repeats n is within the range of $2 \leq n \leq 100$. Preferably, n is up to 25, more preferably n is up to 15, even more preferably n is 10.

Preferably, the peptides of the present invention form a left-handed helix or any other structure with similar function.

Wherein the function is the potential to bind and scavenge methylglyoxal and other RCS in vivo and in vitro, and/or antagonize and/or compete with methylglyoxal and other RCS for binding to proteins, preferably arginine- or lysine-containing (cellular) proteins, such as the sodium ion channel Na(v)1.8, and/or prevent the modification of proteins, preferably arginine- or lysine-containing (cellular) proteins, such as the sodium ion channel Na(v)1.8, by methylglyoxal and other RCS, and/or inhibit and/or prevent the formation of advanced glycation endproducts (AGEs) by methylglyoxal and other RCS.

The number of repeating units of the GEXP motif (n) that would be present within the peptide(s) is dependant upon the scavenging potential to be achieved.

The "scavenging potential" as used herein can be viewed as the amount of methylglyoxal which can react with a GEXP motif-containing peptide of the invention and therefore be the effective amount of methylglyoxal or similarly acting reactive metabolites (such as reactive carbonyl species (RCS)) which are removed from binding to arginine- or lysine-containing (cellular) proteins at any situation in which methylglyoxal or similarly acting reactive metabolites (such as reactive carbonyl species (RCS)) are elevated.

In the example disclosed herein (GEXP motif-containing peptide designated GERP001) ten repeats of the GEXP motif with X=R (ca. 40 amino acids) were utilized, therefore giving a total of ten arginine residues per molecule of peptide. Administration of 1 mg of GERP001 (1 mg$\equiv$$1.096\times10^{15}$ arginine residues) by intraperitoneal injection to healthy wild-type mice, 30 min prior to injection of methylglyoxal (70 μM), reduced methylglyoxal-induced hyperalgesia by approx. 60%. The length of GERP001 was dictated, firstly, by the relative scavenging potential that would be offered from ten arginine residues, and secondly, the relative cost and ease of synthesis. GERP001 represents a preferred and efficient balance between these two factors. For the purpose of this invention, the total number of GEXP motifs (n) with a peptide(s) can be within the following range: $2 \leq n \leq 100$.

Preferably, the peptides according to the present invention have a length of at least 8 amino acids, preferably have a length from about 8 to about 500 amino acids, more preferably about 8 to about 250, even more preferably 10 to 50 amino acids.

In one embodiment, the peptides consist of any length in the range from 8 to about 500 amino acids, preferably from 10 to about 50 amino acids, such as 10, 11, 12, 13 . . . , 44, 45, 46, 47, 48, 49, 50 amino acids. It should be noted that " . . . " denotes every integer in the respective range.

In a preferred embodiment, the compounds according to the present invention further comprise

- tag(s) and/or label(s),
- and/or
- linker,
- and/or
- drug(s), such as small molecules with a pocket binding methylglyoxal.

Tag(s) and Label(s)

Within the context of this invention a "tag" or a "label" refers to (but is not exclusively limited to) the following:

- Affinity or purification tags:
  - such as a His tag or poly(His) (e.g. 6×His), chitin binding protein (CBP), maltose binding protein (MBP), and glutathioine-5-transferase (GST),
- Solubilisation tags,
  - such as thioredoxin (TRX) and poly(NANP),
- Cell permeability tags,
- Chromatography tags,
  - such as FLAG-tag,
- Epitope tags,
  - such as V5-tag, c-myc-tag, and HA-tag.
- Antibodies or antibody fragment tags,
  - preferably through linkage of the e.g. N-terminus of the GEXP motif, via a crosslinker, such as succinimidyl 4-[N-maleimidomethyl] cyclohexane-1-carboxylate (SMCC) and N-succinimdyl 3-(2-pyridyldithio) propionate (SPDP), to the sulfhydryl groups of the antibody of interest,
- Fluorescence tag(s) or label(s)
  - such as green fluorescent protein (GFP) and its derivatives (EGFP, CFP, ECFP, YFP, EYFP, etc), zoanFP or the red fluorescent protein drFP583 and their derivatives,
  - as well as
  - fluorescent dyes,
  - such as Alexa dyes, derivatives of rhodamine and fluorescein, Cy-dyes,
- Radioisotope(s),
  - for in vivo imaging, such as $^{18}F$, $^{67}Ga$, $^{81m}Kr$, $^{99m}Tc$, $^{111}In$, $^{123}I$, $^{133}Xe$, and $^{201}Tl$;
  - for therapy, such as $^{90}Y$ and $^{131}I$,
- Contrast agent(s)
  - such as Gadolinium (Gd) complexes, supramagnetic iron (Fe) complexes and particles, compounds containing atoms of high atomic number, i.e. iodine for computer tomography (CT), microbubbles and carriers such as liposomes which contain these contrast agents, A preferred tag is a His tag or poly(His), e.g. 6×His or $(His)_6$.

Preferably, the compound(s) of the present invention comprises at least one tag (or label).

The tag(s)/label(s) are preferably suitable for an in vivo medical use as known to the skilled artisan.

The skilled artisan will be able to select the respective suitable tag and/or label depending on the respective application.

Linker

In an embodiment of the invention, the compounds comprise linker or spacer, in particular when the compounds also comprise further components, such as tag(s), label(s), drug(s).

Within the context of this invention a "linker" refers to a short sequence of residues (natural or synthetic, such as amino acid residues) which is chemically inert towards either the function of the chosen "tag"/"label" or further component of the compound of the invention. In essence, the "linker" acts as a spacer between the "tag"/"label" (or further component) and the compound (such as the GEXP motif of a peptide), thereby preventing any negative interactions which may arise from the chosen "tag"/"label" (or further component) and the compound (such as the GEXP motif of a peptide).

Preferred linkers can include, but are not exclusively limited to polyalanine, polyglycin, carbohydrates, $(CH_2)_n$ groups. The skilled artisan will, thus, be able to select the respective suitable linker(s) or spacer(s) depending on the respective application A preferred linker is a Gly-rich sequence, such as $(Gly)_4$.

Drug(s)

The drug(s) are preferably small molecules which preferably comprise a pocket that binds methylglyoxal or other RCS.

A preferred embodiment of the present invention is a peptide consisting of the GEXP motif and optionally a tag and/or a linker.

A preferred embodiment of the present invention is the following peptide:

$N'$-$[Tag]_m$-Linker-[Gly-Glu-X-Pro (SEQ ID NO: 1)$]_n$-C' wherein

X is Arg or Lys m is at least 1, preferably 1, n is at least 2, preferably 10,

N' denotes the N-terminus, and

C' denotes the C-terminus.

Please see also FIG. 5A.

Such a preferred peptide according to the present invention contains

- an N-terminal His tag $(His)_6$;
- ten repeats of the GEXP motif with X=Arg $(GERP)_{10}$;
- and a linker or spacer between the His tag and the GEXP motifs $(Gly)_4$;

i.e. it has the following general formula $N'$-$[(His)_6]_1$-$(Gly)_4$-[Gly-Glu-Arg-Pro (SEQ ID NO: 1)$]_{10}$-C"

Such a preferred peptide (also designated GERP001) according to the present invention comprises or has the amino acid sequence with SEQ ID NO. 2

HHHHHHGGGGGERPGERPGERPGERPGERPGERPGERPGERPGERPGERP.

In a preferred embodiment, the compounds according to the present invention comprise N-terminal and/or C-terminal modification(s).

Preferably the N-terminal and/or C-terminal modification(s) comprise acetylation and/or amidation of the N- and/or C-terminus, respectively, i.e. of the respective last amino acid residue, but comprises also the modification in close proximity to either N- or C-terminus, such as the last but one amino acid residue, the last but two amino acid residue or more amino acid residues.

N-terminus acetylation preferably includes acylation with carboxylic acids, fatty acids (saturated or unsaturated fatty acids, branched or unbranched fatty acids, preferably with 8 to 22 carbon atoms), and amino acids with lipophilic side chains (valine, leucine, isoleucine, methionine, phenylalanine). Examples are acylation with myristoyl (C14), palmitoyl (C16) or stearoyl (C18).

Hydrophobic modification of the N-terminus is preferably selected from, but not exclusively limited to, the addition of cholesterol, derivatives of cholesterol, phospholipids, glycolipids, glycerol esters, steroids, ceramids, isoprene derivatives, adamantane, farnesol, aliphatic groups, and polyaromatic compounds.

The attachment of the hydrophobic moieties is preferably by covalent binding, which can be achieved via carbamate, amide, ether, disulfide or any other linkage that is within the skill of the person skilled in the art.

C-terminus modifications include, but are not exclusively limited to, modification(s) with amides, D-amino acids, modified amino acids, cyclic amino acids; natural and synthetic polymers, such as PEG, glycane.

Modifications of either the N- and/or C-terminus or both are preferred because they remove the additional electrical charge that would result from the free amino and carboxy termini of a peptide of the present invention generated during synthesis. In doing this, the resulting peptide(s) will mimic natural occurring peptides and cell permeability increases. Furthermore, stability towards digestion by aminopeptidases is enhanced and further modification by synthetase inhibited.

The skilled artisan will be able to select the respective suitable N- and/or C-terminus modification(s) depending on the respective application.

The peptides of the present invention can furthermore comprise modified amino acid(s), unnatural amino acid(s) or peptidomimetic(s) in their amino acid sequence.

The peptides of this invention can be prepared by a variety of procedures readily known to those skilled in the art, in general by synthetic chemical procedures and/or genetic engineering procedures.

Synthetic chemical procedures include more particularly the solid phase sequential and block synthesis [51]. The solid phase sequential procedure can be performed using established automated methods such as by use of an automated peptide synthesizer. The peptides of the present invention may also be obtained by coupling (poly)peptide fragments that are selectively protected, this coupling being effected e.g. in a solution. The peptides can further be produced by genetic engineering techniques as known to the skilled artisan, utilizing eukaryotic and/or prokaryotic expression systems.

As discussed above, the extracellular matrix (ECM), of which collagen is the most abundant component, has been extensively studied in respect to post-translational modifications by methylglyoxal. It has been proposed that under conditions of hyperglycaemia and altered glucose metabolism, such as in diabetes mellitus, there is an excess generation of methylglyoxal which subsequently modifies key arginine residues in collagen, specifically the GFOGER and RGD integrin binding sites, causing endothelial cell detachment, anoikis and inhibition of angiogenesis.

Collagen contains three polypeptide strands each consisting of two repeating motifs, either Gly-Pro-Y or Gly-X-Hyp, where X and Y may be any other amino acid residue. The high content of proline and/or hydroxyproline, with their geometrically constrained carboxyl and (secondary) amino groups, results in the tendency of the individual polypeptide chains to form left-handed helices spontaneously, without any intrachain hydrogen bonding. Collagen, with its simple structure and subsequent high potential for modification, therefore represents an ideal model for the construction of a synthetic peptide scavenger of methylglyoxal.

In a preferred embodiment a compound of the invention is a GEXP motif-containing peptide that is based upon the repeating motif of the four amino acids; glycine (Gly), glutamate (Glu), arginine (Arg) and proline (Pro) (GERP). As described above for collagen, when multiple units of this motif are linked, they give rise to left-handed helix. The Arg residue within the GERP motif can be considered as the active site and the residue which would scavenge the free methylglyoxal, namely through interaction of the free amino ($NH_2$—) group, to form the methylglyoxal-derived hydroimidazolone (MG-H1).

To ensure that the Arg would be the most reactive towards methylglyoxal, the following rules were applied to its positioning:

- the arginine was positioned such that when multiple units of GERP were linked, each arginine within the repeating motif would be within close proximity to each other (3 residues distance) as to decrease the pKa of both interacting amino groups within the arginine side-chain which would interact with methylglyoxal,
- To facilitate this, the arginine was positioned next to a glutamic residue, as the carboxylate sidechain can act as a catalytic base, in the subsequent reaction with methylglyoxal.
- Glutamic acid was chosen rather than aspartic acid because peptides that contain multiple aspartic acid residues have low stability as they are very susceptible to dehydration to form a cyclic imide intermediate, which can result in cleavage of the peptide chain.

In a preferred embodiment the GEXP motif-containing peptide consists of 50 amino acids in total and has the following sequence:

```
GERP001
                                              SEQ ID NO. 2
HHHHHHGGGGGERPGERPGERPGERPGERPGERPGERPGERPGERPGERP
```

Of these, 40 amino acids represent ten repeats of the GERP motif, therefore giving a total of ten Arg residues per molecule of peptide (1 mg of GERP peptide≡$1.096\times10^{15}$ Arg residues). The length of the peptide was dictated firstly, by the number of Arg residues and in turn scavanging potential, and secondly the relative cost and easy of synthesis. Selection of the peptide containing ten arginine residues therefore represents the most efficient balance between these two factors.

The presence of an additional ten amino acids is the result of linking the core structure of the peptide (the ten GERP motifs) to a His-tag by glycine linkers at the N-terminus. While the His-tag does not add or detract from the scavanging potential, it does provide and effect means by which the peptide can be isolated from physiological samples, such as plasma, serum or culture medium, and the state of modification by methylglyoxal assisted through proteomic techniques.

Further modifications to the GEXP motif-containing peptides of the invention include the modification of the N- and C-terminus, preferably acetylation and/or amidation of the N- and C-terminus, respectively. These modifications are made in order to remove the additional electrical charge that would result from the free amino and carboxy termini generated during synthesis. In doing this, the peptides mimic natural occurring peptides and cell permeability increases. Furthermore, stability towards digestion by aminopeptidases is enhanced and further modification by synthetase inhibited.

Use of the Compounds as Methylglyoxal Scavenger and/or Antagonist

As outlined above, the present invention provides the compounds of the present invention as scavenger of methylglyoxal and/or reactive carbonyl species (RCS).

As it has been discussed above, methylglyoxal and/or RCS will react in physiological systems with protein residues, particularly arginine, to form the advanced glycation end-product, MG-H1. See also FIG. 1. The formation of this modification can alter protein conformation and consequently its function, which is exemplified by the post-translational modification of collagen in the GFOGER and RGD integrin binding sites by methylglyoxal, which results in endothelial cell detachment, anoikis and inhibition of angiogenesis.

The GEXP motif-containing peptide(s) as preferred embodiment of the invention has the potential to react with methylglyoxal, to form MG-H1, but unlike collagen, AGE modification of the GEXP motif-containing peptide(s) will not lead to any deleterious consequences, as the synthetic peptide merely provides an alternative and highly reactive platform for modification by methylglyoxal, due largely to the GEXP motif. The GEXP motif-containing peptide(s) (the compounds of the invention) can, therefore, be viewed as a thermodynamic trap for methylglyoxal produced endogenously within a physiological system, preventing the formation of physiologically derived AGEs. The compounds of the present invention function in the same way.

In the context of this invention, the term "scavenger" of methylglyoxal and/or "scavenging" methylglyoxal, therefore refers to the potential of the compound (such as the GEXP motif-containing peptide(s)) to prevent the interaction of methylglyoxal (or similarly acting reactive metabolites, such as reactive carbonyl species (RCS)) with protein residues, specifically arginine residues or also lysine residues, in proteins, on and/or in macromolecular protein structures and physiological proteins, which includes but is not exclusively limited to voltage-gated sodium channel 1.8 ($N_v$1.8), in vitro as well as in vivo.

The compounds of the invention are suitable as in vitro as well as in vivo scavengers of methylglyoxal and/or reactive carbonyl species (RCS).

Since MG is known to interact with arginine and lysine residues to form stable posttranslational modifications of proteins (49), the inventors, therefore, explored the possibility to reduce noxious MG levels by designing a molecular scavenger able to quench the toxic metabolite. As displayed in FIGS. 5 A and B, the inventors constructed the arginine-rich peptide GERP to bind MG and a control peptide of similar structure but devoid of arginine (GEAP), as described herein. The GERP peptide is uniquely equipped for scavenging free MG, due to a 10-fold glycine, glutamate, arginine and proline repeat. The presence of multiple arginine residues in union with adjacently positioned glutamate residues, acting as a catalytic base, provides an ideal thermodynamic trap for MG, allowing for the formation of MG-derived AGEs such as MG-argpyrimidine (MG-Argpyr), MG-derived hydroimidazolene (MG-H1) and $N^{\varepsilon}$(carboxyethyl)lysine (CEL). When administered systemically, GERP successfully inhibited thermal hyperalgesia not only in healthy wild-type mice treated 3 h before with MG (see FIG. 6A) but also in mice after 8 weeks of diabetes displaying manifest hyperalgesia (see FIG. 6C). In contrast, application of GEAP as an appropriate control had no effect on thermal hyperalgesia in MG-treated (FIG. 6A) or diabetic mice (FIG. 6C). The effect of a single injection (1 mg) of GERP has a half-life of 80 h, indicating that the posttranslational protein modifications by MG do not only rapidly induce hyperalgesia but also constitute a sustained hyperalgesic memory imprint. Thus, the scavenger strategy provides new therapeutic options in treating symptoms of diabetic neuropathy. These data further show that MG interacts with proteins involved in nociceptive processing to induce thermal hyperalgesia.

As outlined above, the present invention provides the compounds of the present invention as antagonist of methylglyoxal for binding to an arginine-containing protein, preferably an arginine-containing (cellular) protein, such as a sodium ion channel, e.g. the sodium ion channel Na(v)1.8.

The inventors have found a modification by methylglyoxal of voltage-gated sodium channel 1.8 ($Na_v$1.8; Scn10a), which is a TTX-resistant channel and presented here as an example of other similarly acting channels. Thus, the function of sodium channel $Na_v$1.8 and the other channels can be modulated by methylglyoxal or similarly acting reactive metabolites (such as reactive carbonyl species (RCS)).

This finding of the inventors provides, for example, a novel mechanism for the development and progression of diabetic neuropathy.

Pharmaceutical Compositions and Medical Applications

As outlined above, the present invention provides a pharmaceutical composition comprising at least one compound as defined herein, preferably at least one GEXP motif containing peptide as defined herein, and optionally a pharmaceutically acceptable carrier and/or excipient.

The pharmaceutical compositions according to the present invention are very well suited for all the uses and methods described herein.

A "pharmaceutically acceptable carrier or excipient" refers to any vehicle wherein or with which the pharmaceutical compositions according to the invention may be formulated. It includes a saline solution such as phosphate buffer saline. In general, a diluent or carrier is selected based upon the mode and route of administration, and standard pharmaceutical practice.

As outlined above, the present invention further provides the first medical use of the compounds of this invention.

Thus, the compounds (such as the GEXP motif containing peptides) of this invention are suitable and, thus, provided for the diagnosis, prevention and/or treatment of diseases.

As outlined above, the present invention further provides the compounds (such as the GEXP motif containing peptides) of this invention and/or respective pharmaceutical composition(s) of this invention for the diagnosis, prevention and/or treatment of certain diseases.

In particular, the compounds (such as the GEXP motif containing peptides) of this invention and/or respective pharmaceutical composition(s) of this invention are suitable for the prevention and/or treatment of pain and/or hyperalgesia.

"Pain" (and/or "hyperalgesia") as used herein refers preferably to pain (and/or hyperalgesia) and/or a disease/condition associated with pain and/or hyperalgesia caused by or associated with methylglyoxal and/or reactive carbonyl species (RCS).

The inventors have found that compounds, which inhibit or antagonize the binding of methylglyoxal (MG) and/or reactive carbonyl species (RCS) to an arginine (or lysine)-containing protein, preferably an arginine (or lysine)-containing cellular protein, such as a sodium ion channel, e.g. the sodium ion channel Na(v)1.8 (the methylglyoxal-scavenging compounds with the characteristics described herein), are suitable for a novel and specific treatment/therapy for pain and/or hyperalgesia, wherein the components causing the pain/hyperalgesia or are associated therewith (namely methylglyoxal (MG) and/or reactive carbonyl species (RCS)) are targeted.

In a preferred embodiment the compounds (such as the GEXP motif containing peptides) or the pharmaceutical composition(s) of the invention are used for the manufacture of a medicament for the prevention and/or treatment of pain and/ or hyperalgesia, in particular pain and/or hyperalgesia caused by or associated with methylglyoxal and/or reactive carbonyl species (RCS).

In a preferred embodiment, the compounds (such as the GEXP motif containing peptides) are provided as analgesic.

The pain and/or hyperalgesia to be prevented and/or treated is associated with and/or occurs during a disease, wherein said disease is selected from Alzheimers disease, amyotrophic lateral sclerosis, cataractogenesis, chronic renal failure and chronic and acute Uraemia, cystic fibrosis, dementia with Lewy bodies, diabetes mellitus and its complications (such as nephropathy, neuropathy and retinopathy), ischaemia-reperfusion, pre-eclampsia, psoriasis, rheumatoid arthritis and juvenile chronic arthritis, severe sepsis, systemic amyloidosis, Parkinson's disease, painful bowel disease, chemotherapy induced pain, critical limb ischemia, hypertension, bone pain, tumor pain.

In diabetes mellitus, neuropathy, which is one of three main major complications associated with the disease, is frequently observed with patients exhibiting one or more types of stimulus-evolved pain, including increased responsiveness to noxious stimuli (hyperalgesia) as well as hyper-responsiveness to normally innocuous stimuli (allodynia). The underlying mechanism of persistent pain diabetic patients remains poorly understood and as such there are little or no effective therapeutic treatments which can either delay or prevent the onset of symptoms.

As discussed above, the formation of methylglyoxal and related reactive carbonyl species (RCS) is closely linked to the rate of glycolysis and the presence of glycolytic intermediates. Hence, in conditions where there is increased glycolytic flux and an increased dependence on glycolysis for energy, the rate of methylglyoxal and RCS formation will also be increased. This has been shown to be the case in patients with diabetes mellitus, where complications such as nephropathy, neuropathy and retinopathy have been linked to increases in cellular levels of advanced glycation endproducts (AGEs). While diabetes has been the main area of research, new evidence is now emerging of the pivot role that RCS, in particularly methylglyoxal, plays in the progression and severity of various diseases. (see Table 1)

For example, methylglyoxal modification of Nav1.8 facilitates nociceptive neuron firing and causes metabolic hyperalgesia:

Small fiber distal polyneuropathy causes persistent hyperalgesia and pain in 10% of people with diabetes. Metabolic hyperalgesia is based on the reactive glycolytic metabolite methylglyoxal (MG). MG exceeding plasma levels of 600 nM discriminates between diabetic patients with and without pain, evokes thermal hyperalgesia in mice and induces CGRP release in skin flaps. Cultured sensory neurons treated with MG exhibit intense MG-modifications of arginine residues in the sodium-channel $Na_v1.8$ and increased electrical excitability and membrane resistance. MG effects on action potential generators facilitate firing in nociceptive neurons but inhibit neurons of the autonomic nervous system lacking $Na_v1.8$ expression. The understanding of metabolic driven pain is useful for therapeutic interventions, since an MG binding peptide is able to reduce hyperalgesia in experimental diabetes, thus providing the first pathogenically based treatment option for painful diabetic neuropathy.

There exists a concept of neuronal dysfunction in certain metabolic diseases. The major insight is the identification (by the inventors) of a key role for local accumulation of the reactive metabolite MG, which by posttranslational modification of the sensory neuronal sodium channel $Na_v1.8$ enhances the excitability and blocks other ion channels including $Na_v1.7$. The concept of metabolic hyperalgesia appears independent of structural changes in the nerve but rather dependent on the molecular interaction of MG with arginine and lysine residues within critical regions of $Na_v1.8$. This observation is compatible with the threshold of about 600 nM MG required to affect neuronal function which was observed in men, mice and peripheral nerve endings. There are several possibilities by which the required MG threshold can be reached. One is the increased metabolic flux of glucose in diabetes through either glycolysis or the pentose phosphate pathway (47). Under non-diabetic conditions, the incidental amount of MG generated is detoxified by protective enzymes, particularly the glyoxalase system. Other pathological states leading to increased generation of MG are disorders in which acetone and other ketone bodies accumulate, such as uremia, or conditions such as oxidative stress during re-perfusion in which lipid peroxidation occurs. See also FIGS. 7 and 8.

Route of Administration

Preferably, the route of administration of the compounds (such as the GEXP motif containing peptides) or pharmaceutical compositions of the present invention is selected from subcutaneous, intravenous, oral, nasal, intramuscular, transdermal, inhalative, by suppository.

A preferred embodiment for nasal administration or application is as an inhalant spray, which would be advantageous for compound(s) (such as the GEXP motif containing peptide(s)), as it would not only allow for faster acting effect, but also limit degradation which may result from oral administration, either from nausea or degradation in the gut or liver.

Therapeutically Effective Amount

The compounds (such as the GEXP motif containing peptides) or the pharmaceutical compositions of the invention are provided such that they comprise a therapeutically effective amount of said compound(s) (such as said GEXP motif containing peptide(s)) of said pharmaceutical composition(s).

A "therapeutically effective amount" of a compound (such as a GEXP motif containing peptide) or a pharmaceutical composition of this invention refers to the amount that is sufficient induce a reduction of ≥50% in clinical symptoms of the treated disease. Within the context of this invention, this includes but is not exclusively limited, to a reduction of 50% in the levels of pain within a patient as determined by the normal clinical parameters.

A preferred therapeutically effective amount is in the range of 10 μg to 1 mg per kg body weight, preferably 10 μg to 100 μg.

The preferred therapeutically effective amount depends on the respective application and desired outcome of inhibition, treatment or prevention.

The skilled artisan will be able to determine suitable therapeutically effective amounts.

Screening Method

The invention further provides a screening method, in particular a method for identifying/screening compounds that influence pain and/or hyperalgesia, in particular pain and/or hyperalgesia caused by or associated with methylglyoxal and/or reactive carbonyl species (RCS).

Said method preferably comprises (a) providing a compound to be screened, (b) providing a compound according to the present invention (as defined herein, such as a GEXP motif containing peptide), (c) determining the effect of the compound to be screened of (a) on the development and/or progression of pain and/or hyperalgesia in a suitable test model.

The skilled artisan will be able to determine and apply a suitable test model.

Such a test model might comprise one or more of the following an arginine-containing protein, preferably an arginine-containing cellular protein, more preferably sodium ion channel Na(v)1.8, and/or methylglyoxal and/or reactive carbonyl species (RCS).

An example of a test model is described in the examples, namely a mouse model.

In such a test model, the compound to be tested may compete with the compound of the present invention for the binding to methylglyoxal and/or another reactive carbonyl species (RCS).

Preferably, the compound of the present invention comprises suitable tag(s) and/or label(s) allowing a detection and determination of the compound to be screened.

The invention further provides the compounds identified in the screening method above.

These compounds are suitable for influencing pain and/or hyperalgesia, in particular pain and/or hyperalgesia caused by or associated with methylglyoxal and/or reactive carbonyl species (RCS)

The following examples and drawings illustrate the present invention without, however, limiting the same thereto.

(A) Hydrophobic moment plot for voltage gated sodium channel $Na_v1.8$, defining the receptor binding domin (RBD). All residues which fall within this region have the potential to participate in glycation-like reactions, in particular lysine (Blue) and arginine (Green) residues.

(B) Subunit structure of the voltage gated sodium channel $Na_v1.8$. Based upon the RDB domain, there are 11 arginine residues and 10 lysine residues located within the structure of $Na_v0.8$ which can be glycated.

(C) Shown are the glycation 'hotspots' of the voltage gated sodium channel $Na_v1.8$-11 Arginine residues, wherein the Arginines residues are in proximity to relevant structures.

Figure 1:
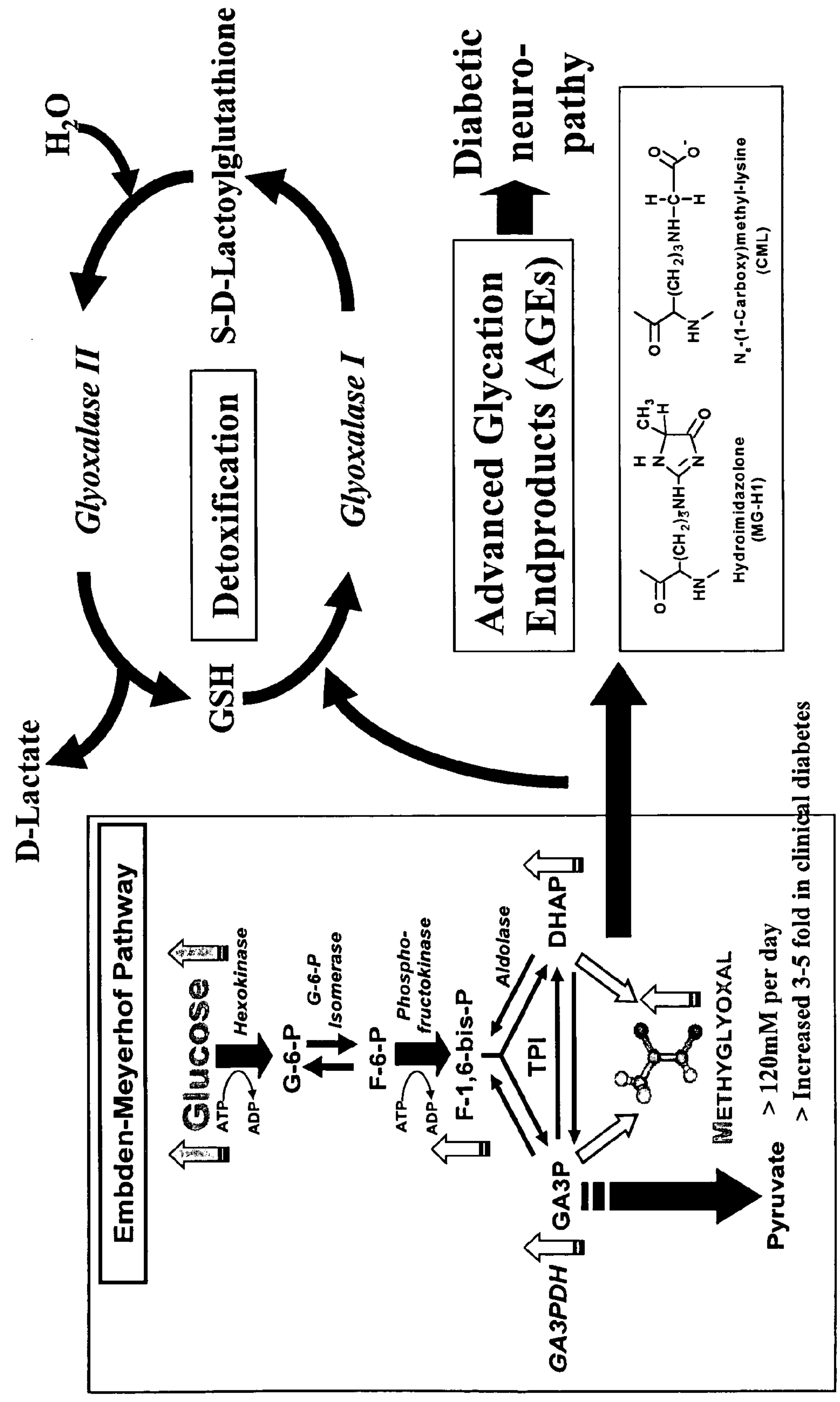
FIG. 1. Formation of Methylglyoxal (MGs) and Advanced Glycation Endproducts (AGEs).
Figure 2:
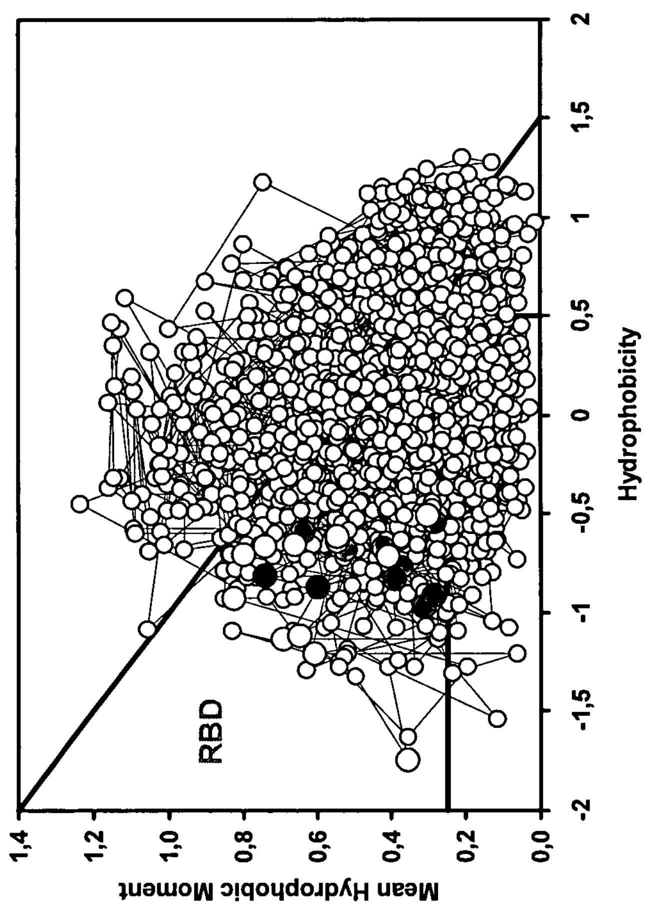
FIG. 2. Molecular Modelling of $Na_v1.8$ Glycation Hotspots.
Figure 2:
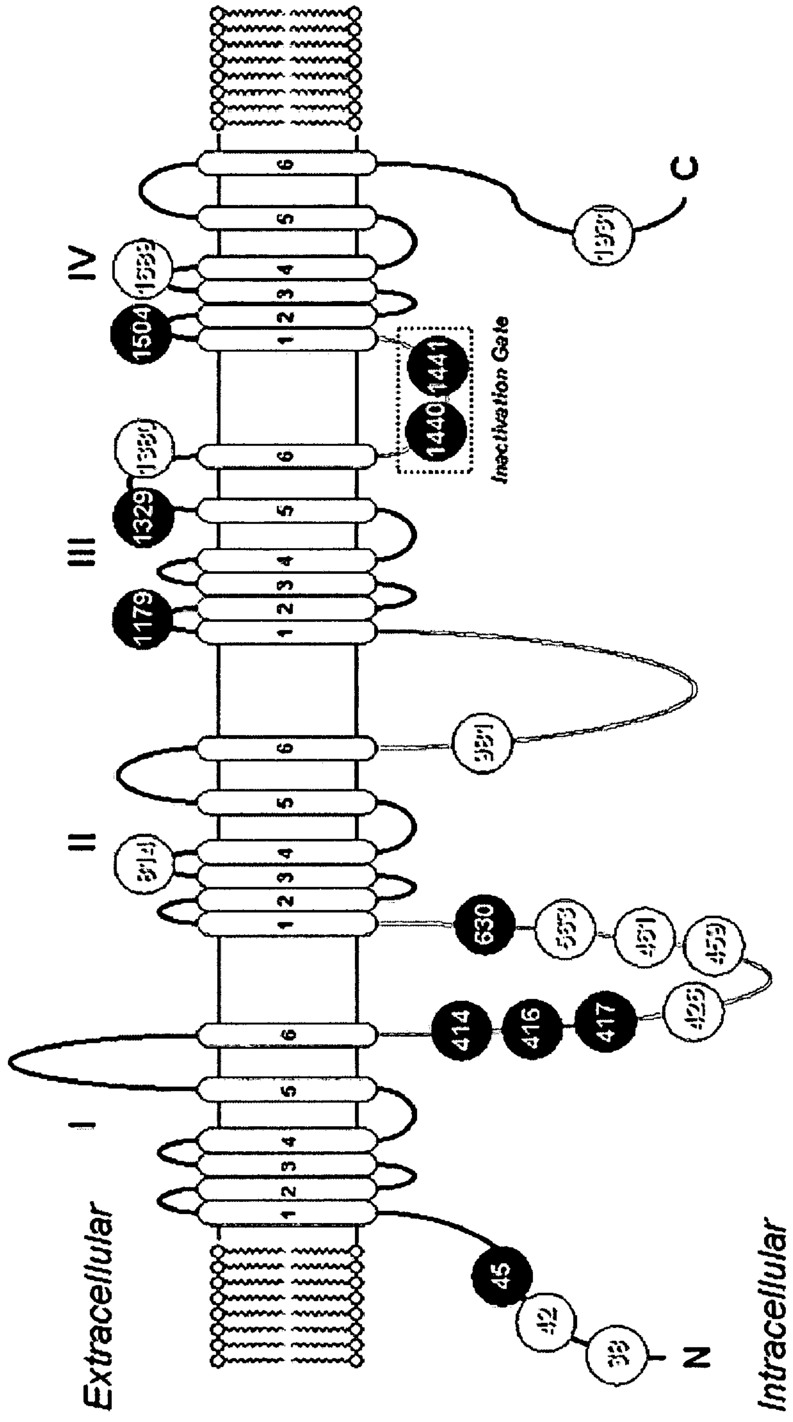
Figure 2:
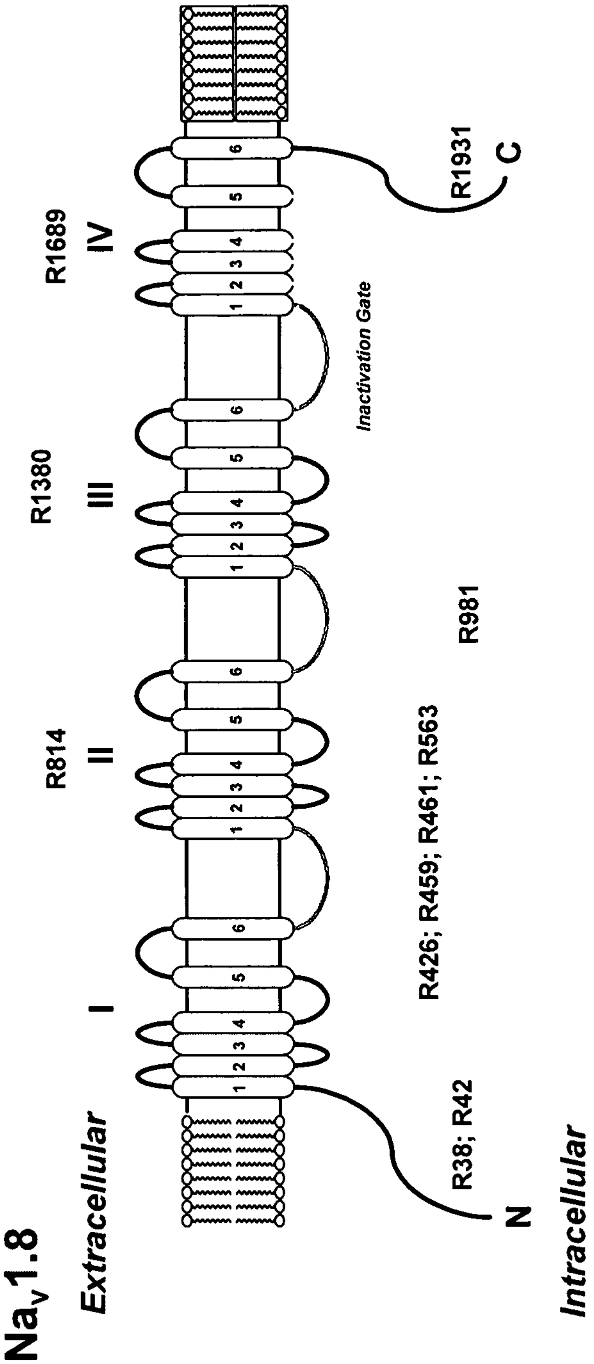
Figure 3:
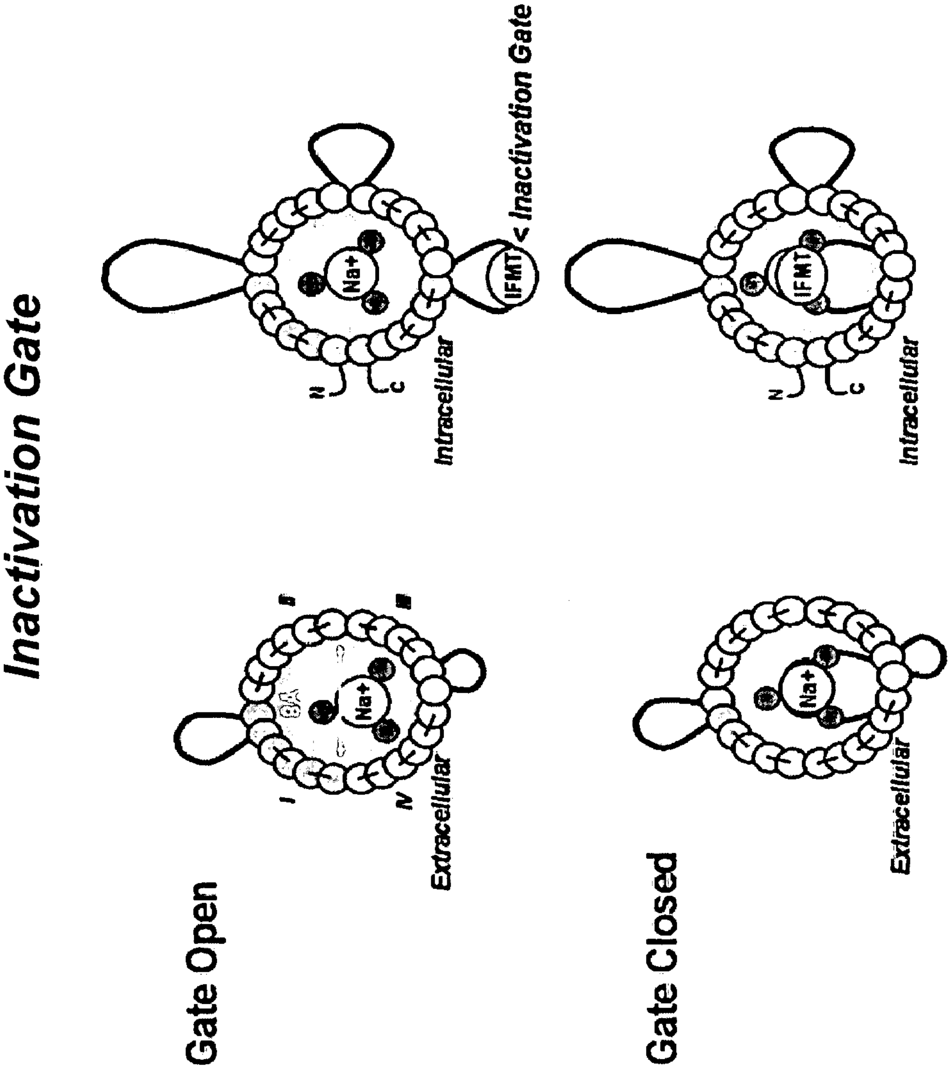
Figure 3:
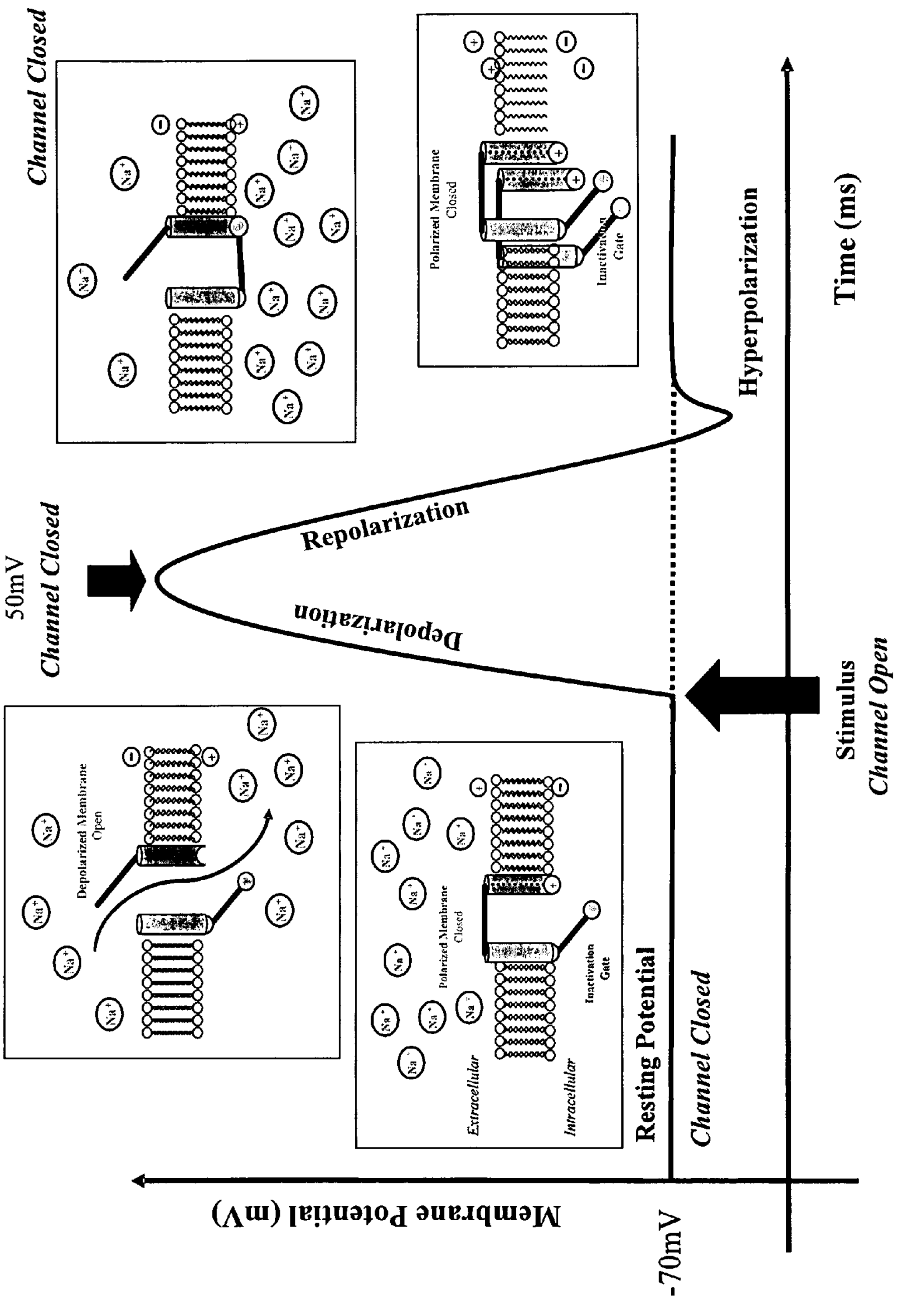
Figure 3:
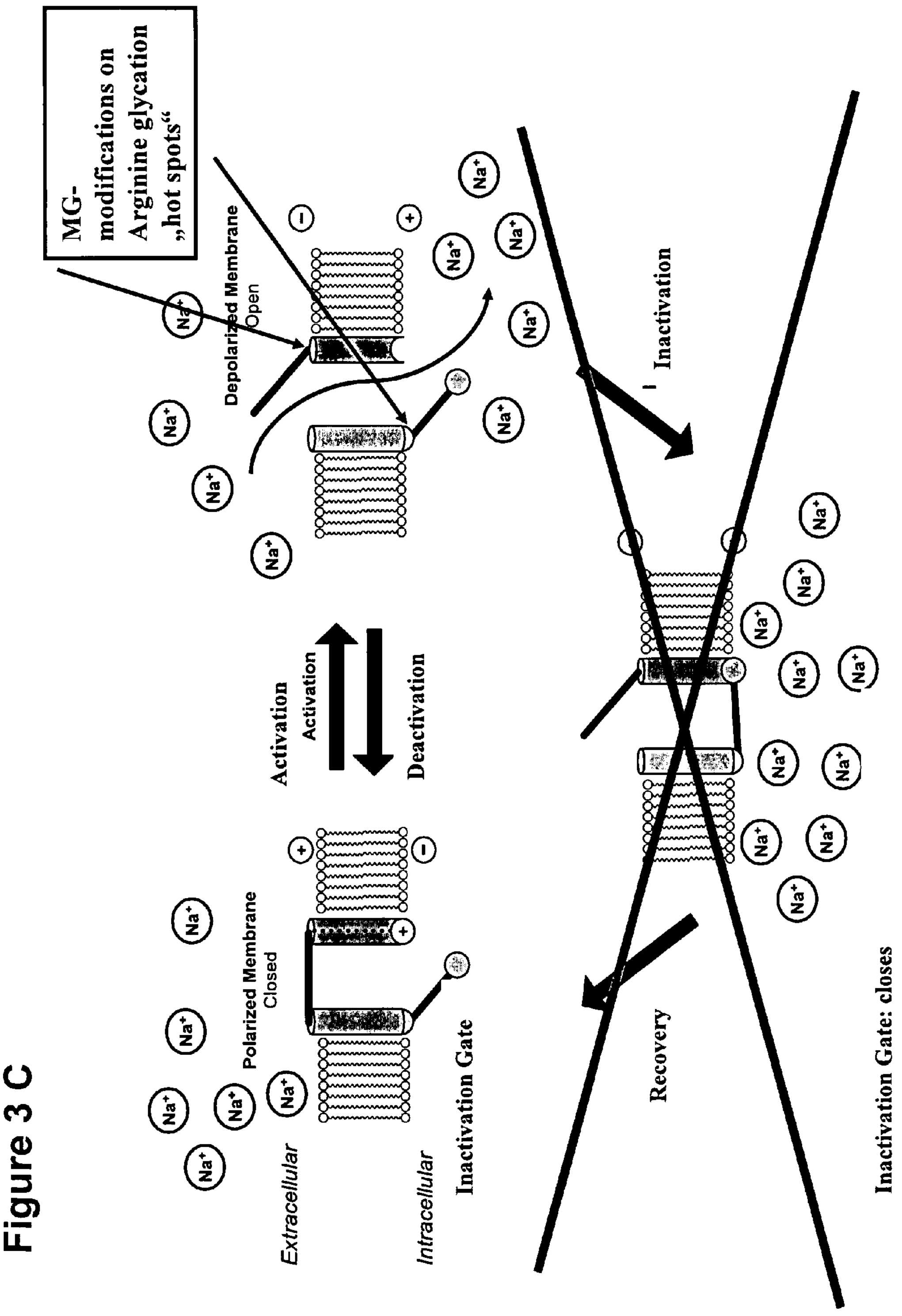

FIG. 3. The Sodium Channel $Na_v1.8$ Contributes to Inflammatory and Neuropathic Pain (A) Inactivation gate of $Na_v1.8$.

(B) Sodium channel: mechanism and action potential.

(C) Posttranslational modification of arginine residues inhibits its closing of $Na_v1.8$.

Figure 4:
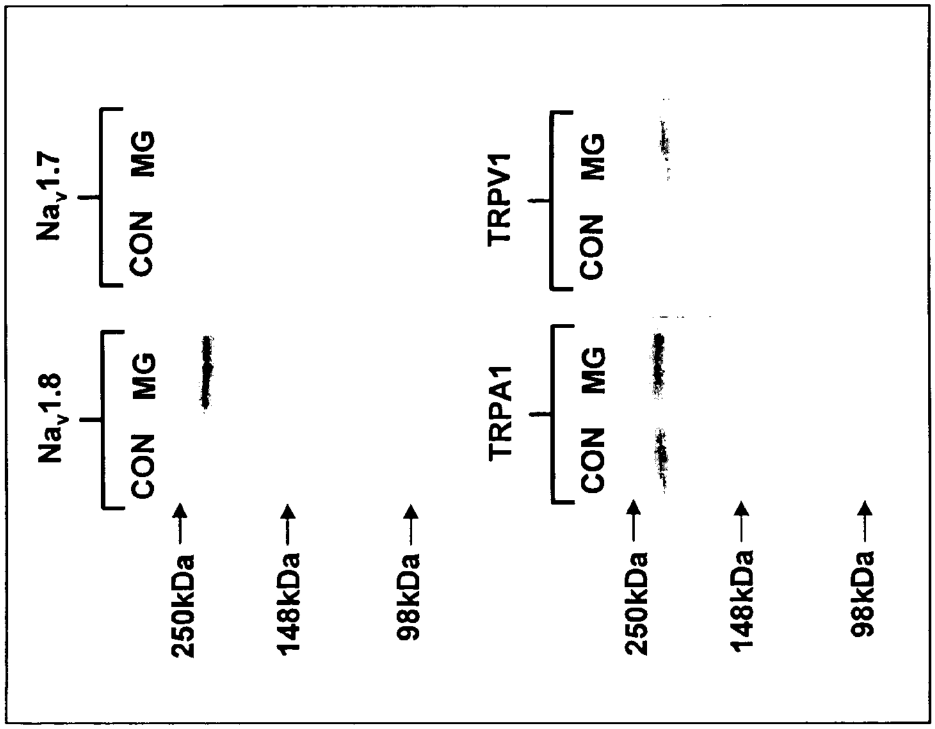
Figure 4:
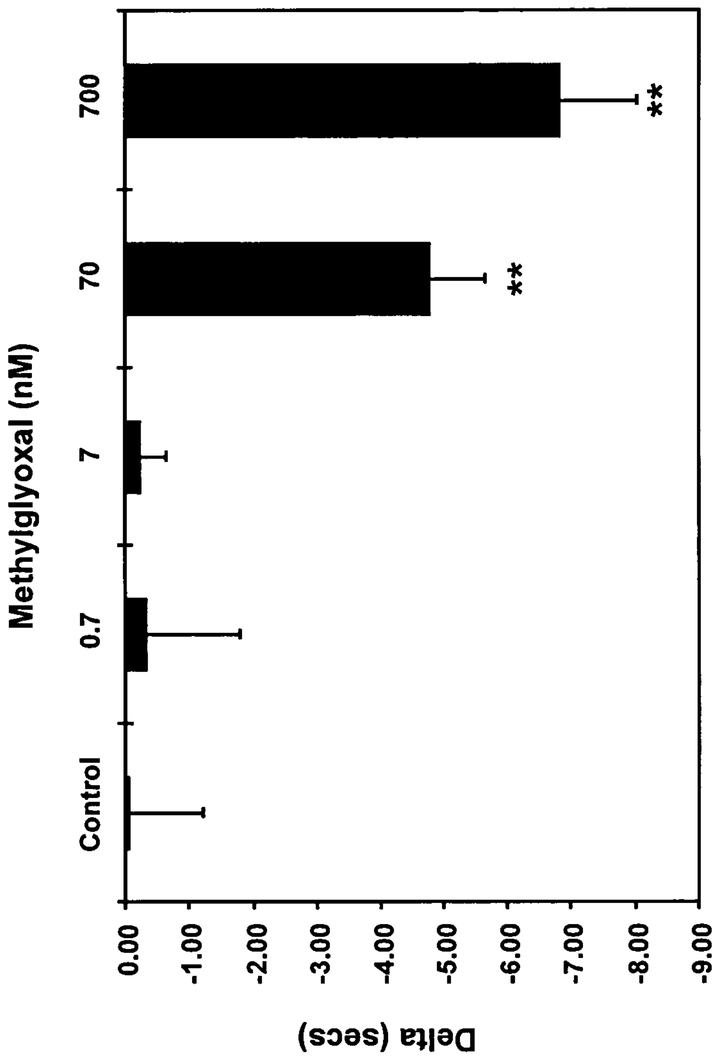
Figure 4:
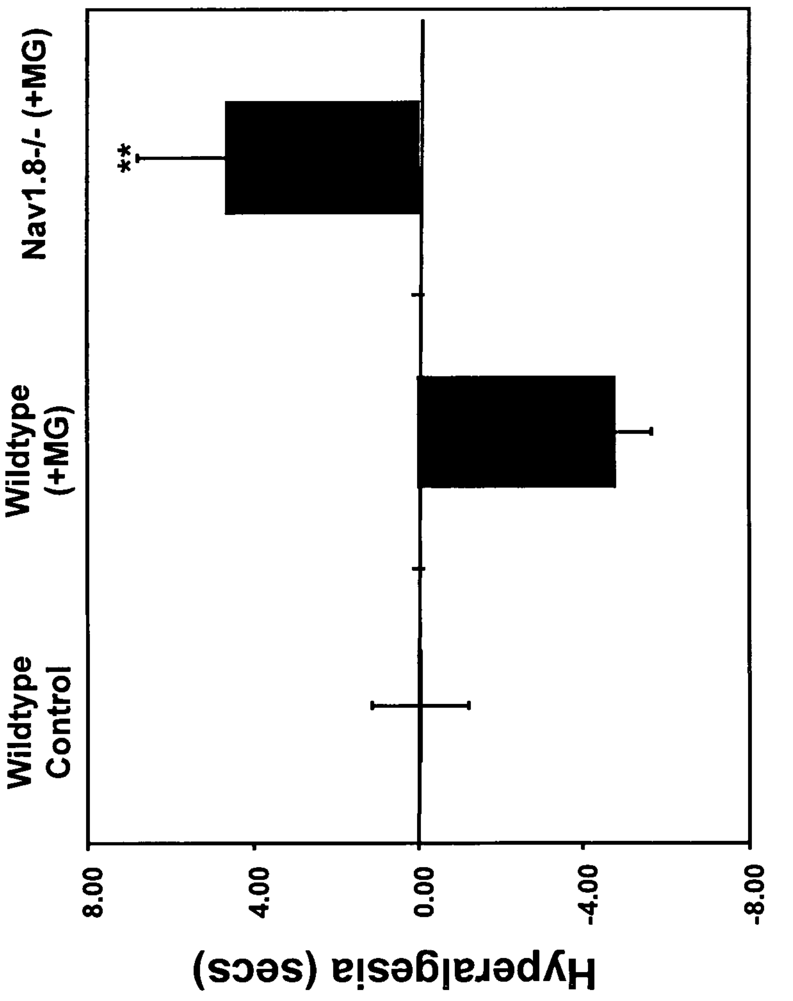

FIG. 4. Effect of Exogenous Methylglyoxal Upon Hyperalgesia.

(A) and (B) Nav1.8 in PC12-Cells is Posttranslationally-Modified by Mg-Derived Adducts:

PC12 cells ($\geq 20\times10^6$ cells) were treated with 40 mM glucose or MG (50, 200 and 500 μM) for 3 h (A) or 4 μM cell-permeable Glyoxalase-1-inhibitor S-p-Bromobenzyl-gluthathione Cyclopentyl diester for 48 h and 72 h respectively (B), before membrane fractions were prepared and immunoprecipitated using antibodies for Nav1.8. Immunoprecipitates were then immunoblotted for MG-derived AGEs. Data represent the mean±SD (n=3).

(C) MG Modification of Membrane Proteins in Dorsal Root Ganglia:

DRGs in the lumbar and thoracic regions of the spinal cord were collected from control and MG-treated (70 μM; i. v., 3 h) Wistar rats. Membrane fractions were prepared and immunoprecipitated using antibodies for Nav1.8, Nav1.7, TRPV1 and TRPA1. Immunoprecipitates were then analyzed by Western Blots with an antibody detecting the MG-derived AGEs.

(D) Exogenous Methylglyoxal Induces Thermal Hyperalgesia In Vivo:

Different concentrations of MG were administered by i.v. injection as 0.9% NaCl solution to male healthy wild-type mice (10-12 weeks). Control mice were injected with only 0.9% NaCl. 3 h after application, thermal hyperalgesiaw as assessed by the Hot Plate assay (bottom). Data represent the mean±SEM (n=10).

(E) Effect of Exogenous Methylglyoxal Upon Hyperalgesia:

Effect of exogenous methylglyoxal upon hyperalgesia, as measured by hot-plate assay in healthy wildtype and Nav1.8−/− mice. Mice were treated with methylglyoxal (i.v. 70 μM). Hyperalgesia and foot withdrawal was assessed 3 hrs after injection. Data represents mean±SD (N=5-6). **P<0.001, NSP>0.05 vs. wildtype(+MG).

Figure 5:
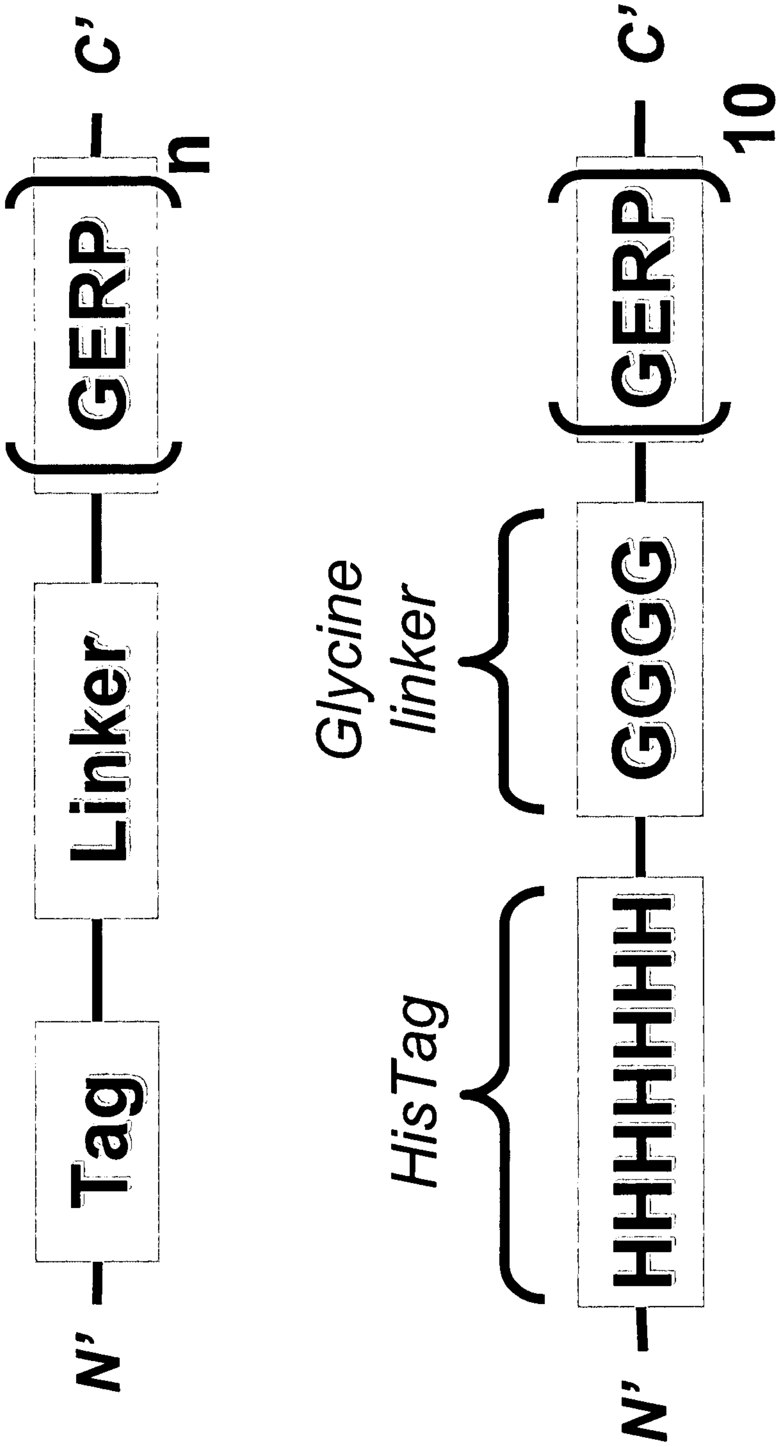
Figure 5:
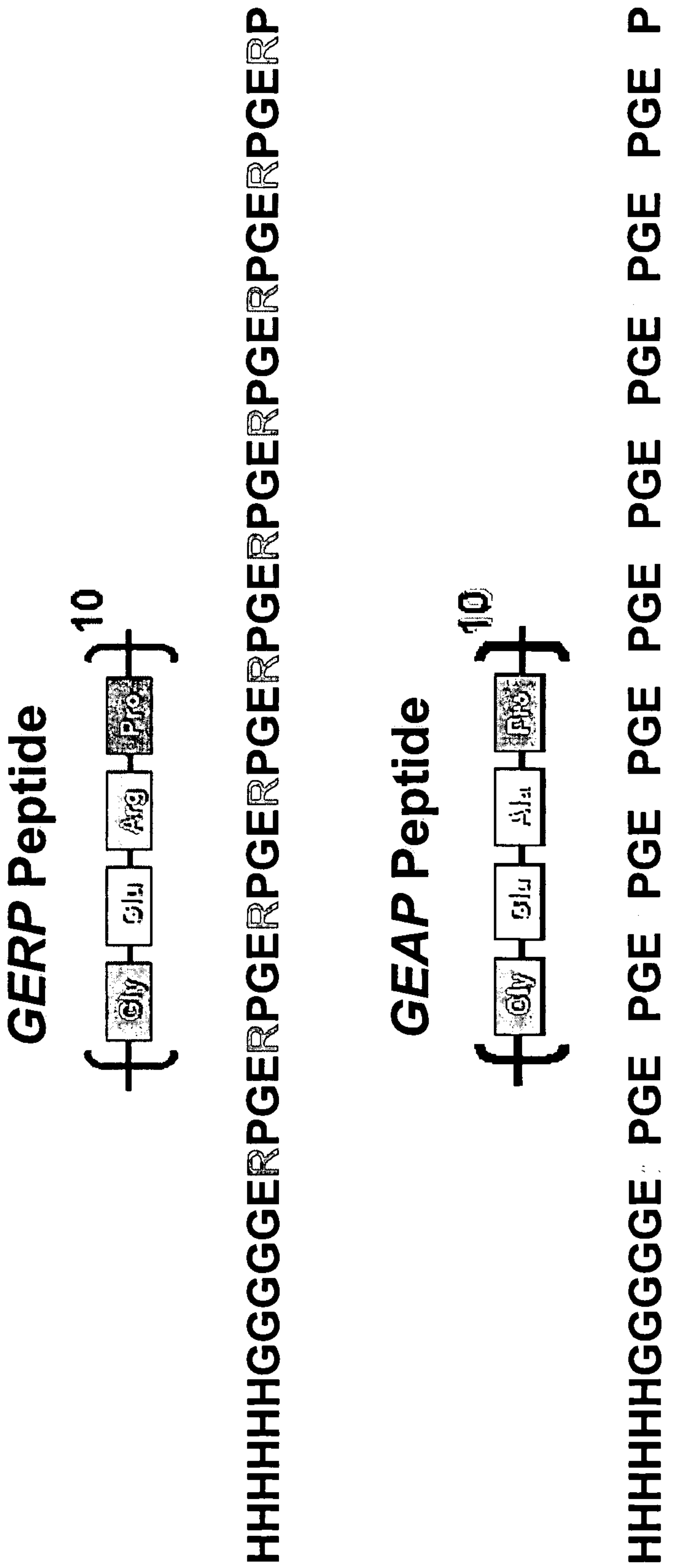

FIG. 5. Design of an Arginine Containing Scavenging Peptide to Antagonize MG-binding to Nav1.8.

A synthetic peptide GERP001 was designed containing ten arginine residues per molecule, to act as an effective in vivo scavanger of methylglyoxal.

(A) General structure of a preferred embodiment of a peptide containing the GEXP or GERP motif according to the present invention (upper part) and example thereof (lower part) (SEQ ID NOs:1, 17, 18).

(B) Primary amino acid sequence of GERP and control peptide (GEAP) SEQ ID NO:19).

Figure 6:
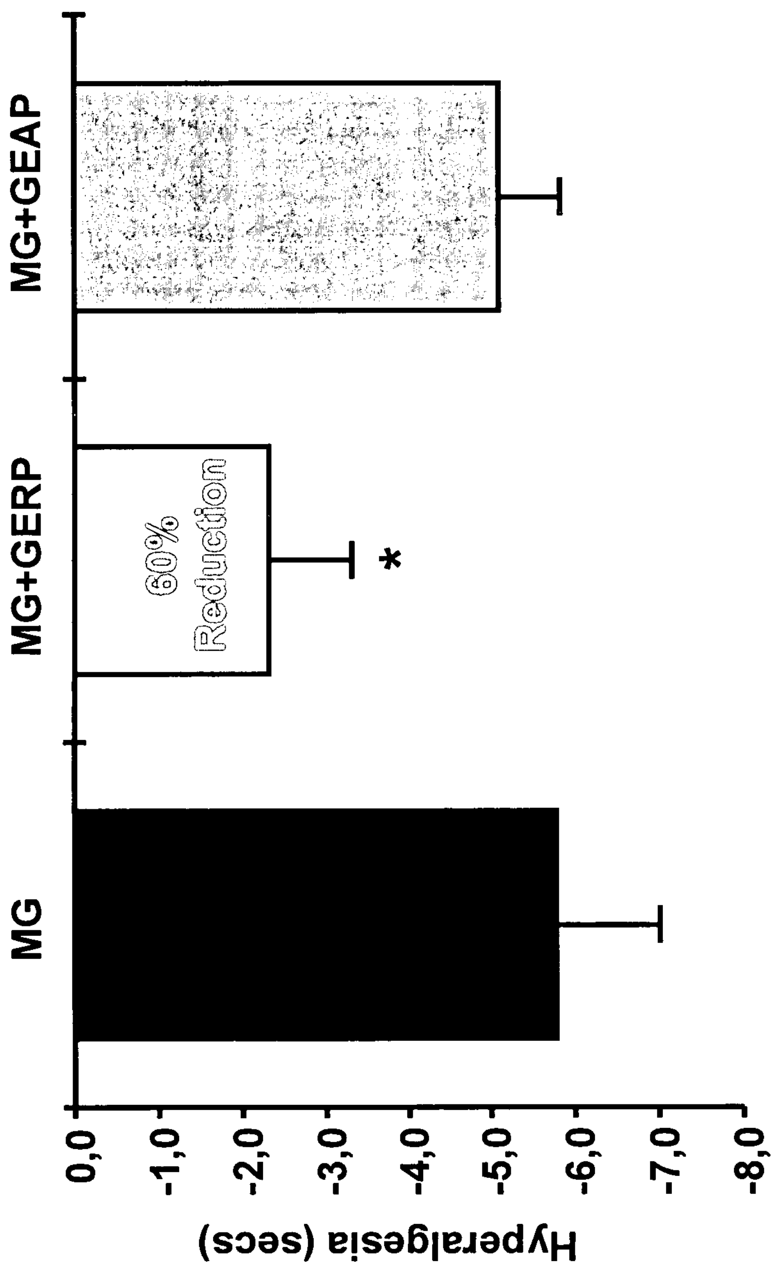
Figure 6:
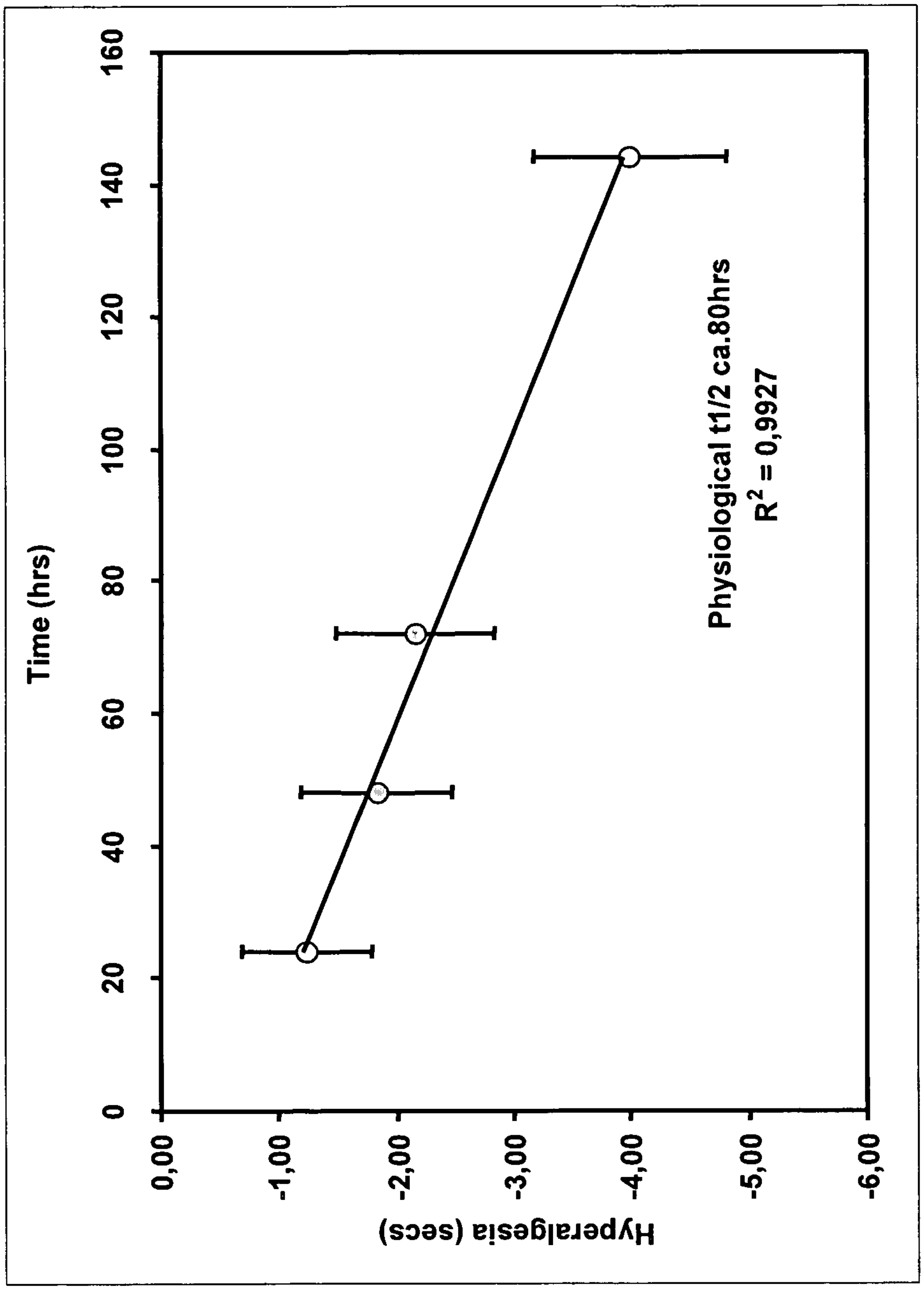
Figure 6:
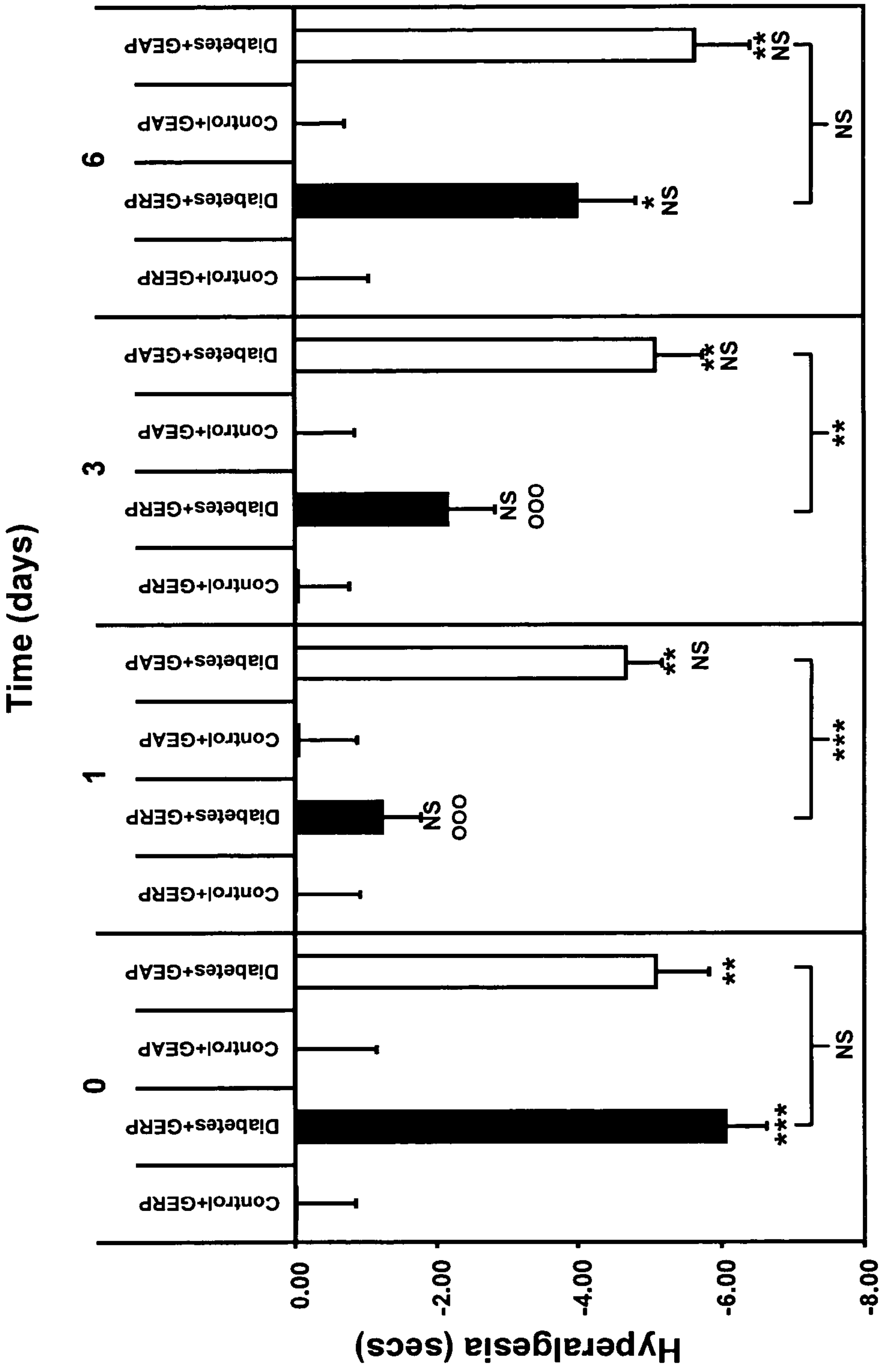
Figure 6:
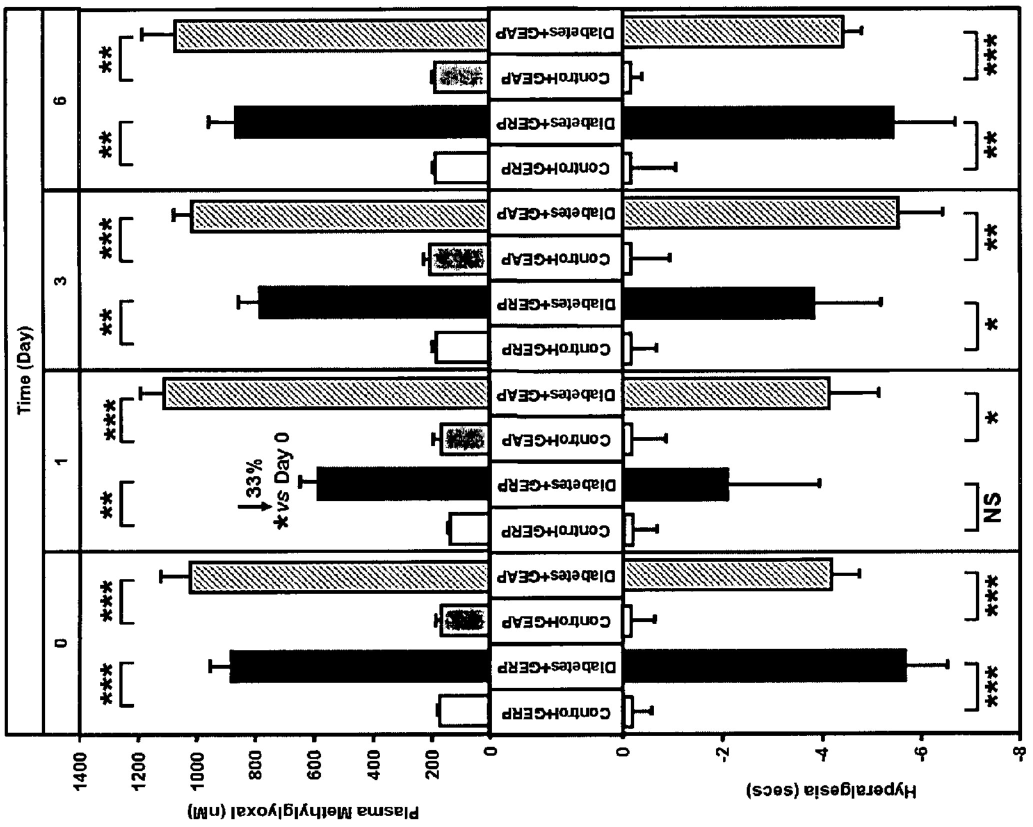

FIG. 6. Effect of Methylglyoxal Scavenging Peptide (GEXP) on Diabetes Induced Hyperalgesia.

(A) Methylglyoxal Scavanging Potential of the GERP Peptide:

Healthy wildtype mice (10-12 weeks), were injected with 1 mg GERP (≡1.096x1015 Arg residues) or control peptide GEAP; i.p. 30 mins prior to injection with methylglyoxal (MG; 70 μM). Hyperalgesia was assessed 3 hrs after i.p injection by hot-plate assay. Data represent mean±SEM (N=10). GERP reduced methylglyoxal-induced hyperalgesia by ca. 60% in healthy wildtype mice, whereas the control peptide had no effect, showing that scavanging of methylglyoxal reduced hyperalgesia.

(B) Effect of Methylglyoxal Scavenging Peptide (GERP) on Diabetes Induced Hyperalgesia:

Graph shows delta for the time point after which treatment with GERP was discontinued. The data for the +24 hr time point was taken as 0. Based on regression analysis, physiological half-life of GERP is ca. 80 hrs. Data represent the mean±SD (N=4-6).

(C) Effect of GERP and GEAP on Diabetes Induced Hyperalgesia:

Diabetic wildtype mice (Male; 18 wks) were injected with either 1 mg GERP or GEAP i.p. Following 1 day of treatment with either peptide, treatment was discontinued, after which consecutive measurements of hyperalgesia were performed to determine biological half-life of the peptide. This was determined to be ca. 80 hrs. Data represent the mean±SEM (N=10), *P<0.0001, P<0.001, *P<0.05, NSP>0.05 vs. GERP or GEAP control at respective time point; 000P<0.0001, NSP>0.05 vs. day 0.

The biological effective half-life (i.e the time taken for the therapeutic effect to reduce by 50%) of the GERP peptide, based upon preliminary experiments, was estimated to be ca. 13 hrs, and was calculated by fitting the data to an exponential decay (R2=0.9734). Following repetition of the initial experiments, which confirmed the validity of the therapeutic potential of GERP peptide, the biological effective half-life of the GERP peptide was again calculated. It was found that the data could not be fitted to an exponential decay ($R2<0.500$), and was best explained by a linear decay model ($R2=0.9972$), which gave an estimated biological effective half-life of ca. 80 hrs.

(D) Effect of Methylglyoxal Scavangering Peptide (GERP) and Control Peptide (GEAP) on Plasma Methylglyoxal in Diabetes (Top) and Diabetes Induced Hyperalgesia (Bottom).

8 week diabetic male wild-type mice (18 weeks old) demonstrating overt hyperalgesia (day 0) received an i. p. injection of either 1 mg GERP or GEAP. Following one day of treatment with either peptide, treatment was discontinued, after which consecutive hotplate assay measurements were performed to determine the effects of MG-scavenging on the diabetes-induced thermal hyperalgesia. Selected mice were sacrificed at each time point and plasma isolated for MG determined by derivatisation with 1,2-diamino-4,5-dimethoxybenezene and HPLC analysis. Data represent the mean±SEM (n=3 per time point).

Figure 7:
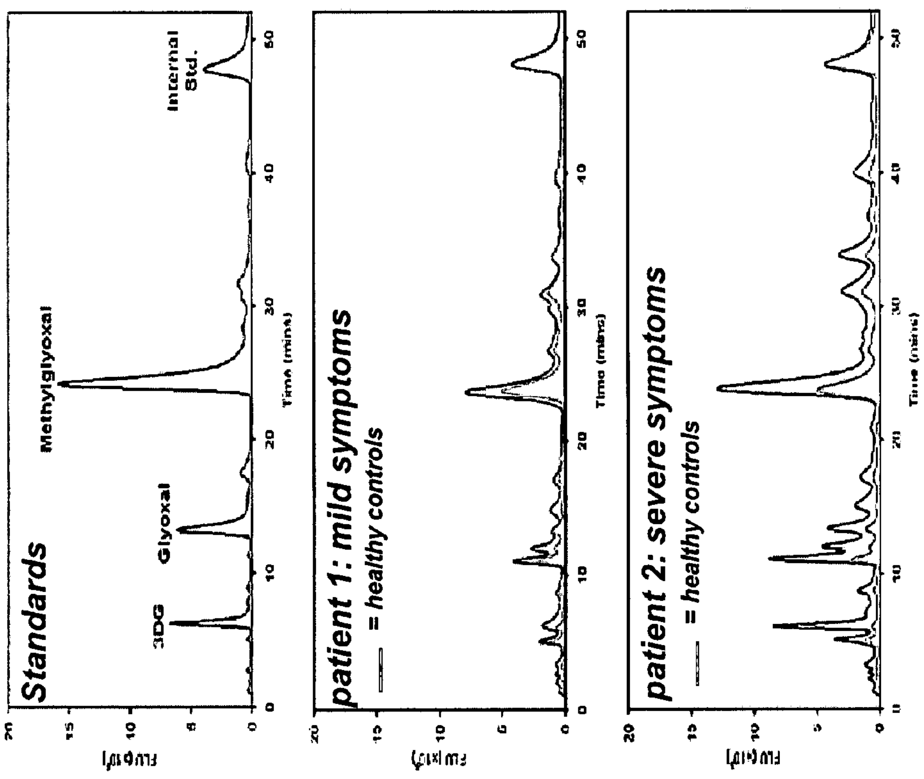
Figure 7:
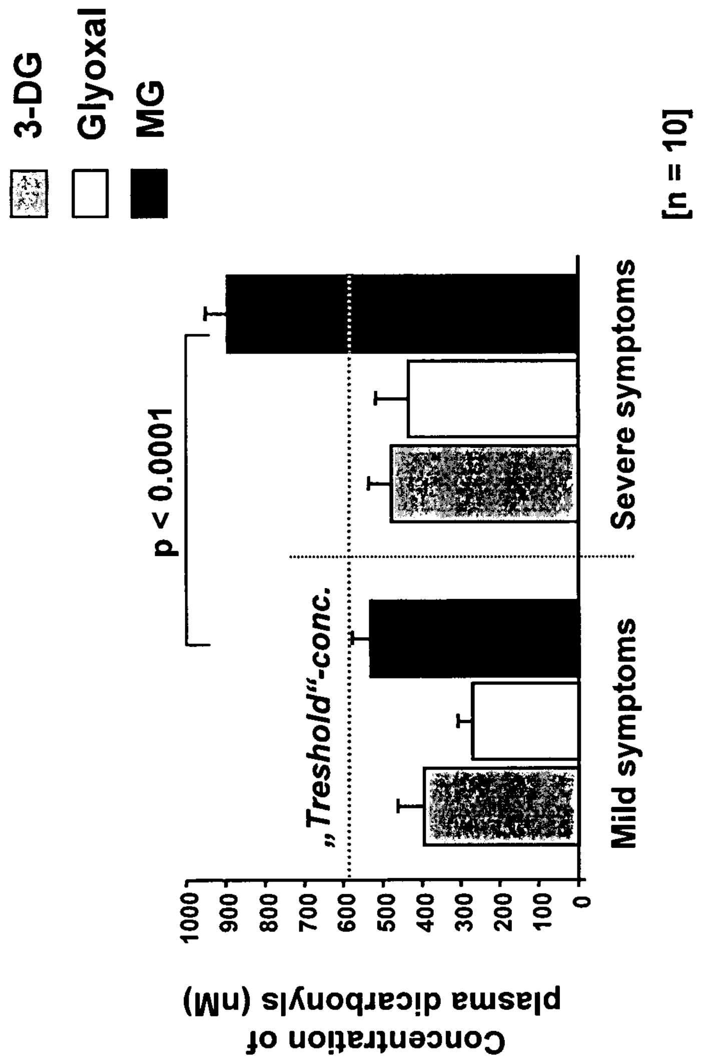

FIG. 7. Methylglyoxal Plasma Levels are Increased in Patients with Symptomatic Diabetic Neuropathy.

(A) Examples of analytical chromatograms identifying soluble mediators increased in the plasma of diabetic patients with severe symptoms: analytical HPLC of standard dicarbonyls (top) and plasma samples from patients with mild (middle) and severe symptoms (bottom). The chromatograms of healthy subjects are inserted as faint grey line.

The HPLC-based characterization of glucose-derived soluble reactive dicarbonyl metabolites in the plasma samples showed elevated dicarbonyl levels in diabetic patients (black lines) compared to healthy controls (grey lines below black lines).

(B) MG plasma concentration in type 2-diabetic patients with mild (black) and with severe symptoms (white). The dashed grey line indicates the MG-threshold concentration at approx. 600 nM. Data represent the mean±SEM (n=10 per group).

When MG plasma levels were determined by HPLC in the patients, a highly significant difference was observed dependent on the absence or presence of symptoms. While MG levels in patients without symptoms were 531±46 nM on average, patients with severe dysesthesia presented with MG plasma levels of 895±55 nM ($p<0.0001$), implying that a certain increase in MG is required to induce pain, and indicate that a threshold MG level is required which, when exceeded, activates a cascade of events causing symptoms.

Figure 8:
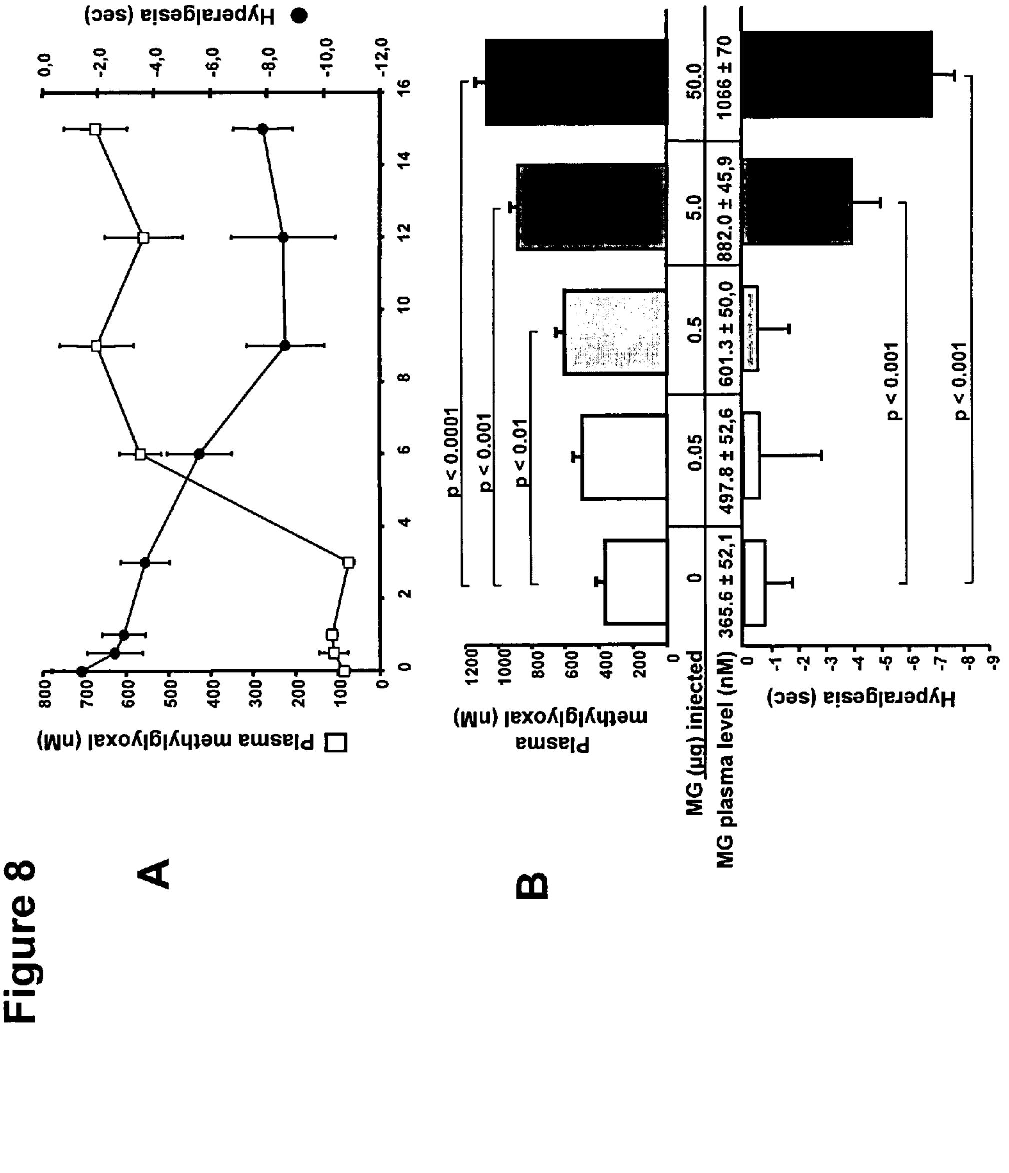

FIG. 8. Exogenous Methylglyoxal Induces Thermal Hyperalgesia In Vivo.

(A) Inhibition of Glyoxalase I by the cell permeable inhibitor S-p-Bromobenzylglutathione Cyclopentyl diester in male healthy wild-type mice (10-12 weeks old). Hyperalgesia was assessed by the hot plate assay at day 0 before application of the inhibitor. Thereafter, consecutive assessments of thermal hyperalgesia were made at selected time points (black circles), at which some mice also were sacrificed and plasma isolated for the determination of MG concentration (open circles). Data represent mean±SD (n=3 per time point). Different approaches were utilized to verify the hypothesized threshold-dependent effect of the MG/glyoxalase-system on hyperalgesia. First, a cell permeable inhibitor (S-p-Bromobenzylglutathione-cyclopentyldiester; of the central and rate-limiting MG-detoxifying enzyme glyoxalase-I was injected every second day into healthy C57BL/6 wild-type mice. This treatment resulted in a time-dependent increase in the plasma MG concentration (open squares). As soon as glyoxalase-I enzymatic activity was fully inhibited 3 days after continuous inhibitor administration, the MG concentration increased. This was paralleled by, an increase in thermal hyperalgesia (black circles). 6 days after initiation of treatment, significant thermal hyperalgesia became evident, while the MG plasma concentration exceeded 600 nM which is comparable to the MG plasma concentration measured in patients with burning pain and tingling dysesthesia.

(B) 5 µg (70 µmoles) MG was administered by i. v. injection as 0.9% NaCl solution to male healthy wild-type mice (10-12 weeks old) and MG-plasma concentrations were determined by HPLC at time point Oh, 10 min, 30 min, 1 h and 3 h. Data represent mean±SD (n=3 per time point).

To confirm that elevated MG levels can directly induce hyperalgesia, 5 µg (70 µmmoles) MG were administered to healthy wild-type mice via i.v. injection. This resulted in an immediate increase in plasma MG levels within 10 min to concentrations above 800 nM (data not shown), a concentration also seen in patients with severe symptoms. Although the plasma MG level returned back to normal within a short time, the systemic administration of MG caused a significant and dose-dependent induction of heat hyperalgesia evident 3 h after MG injection as assessed by hot plate (FIG. 8B, Hargreaves (data not shown) and tail flick tests (data not shown). Most importantly, a dose-dependent hyperalgesia after MG application occurred only if plasma MG levels at 15 min exceeded 600 nM (FIG. 8B), suggesting a threshold concentration for inducing metabolic hyperalgesia. Since the MG-induced changes resulting in hyperalgesia persisted for more than 3 hours (data not shown) and at time points at which MG levels had returned to normal, these data show that a dose-dependent covalent protein modification by MG is the initiating factor leading to thermal hyperalgesia.

EXAMPLES

Methods

Mouse Models.

Mice were housed individually with a 12-hour/12-hour light/dark cycle and free access to food and water. Procedures in this study were approved by the Animal Care and Use Committees at the Regierungspräsidien Tübingen and Karlsruhe, Germany.

Induction of Diabetes using STZ.

Diabetes was induced by i.p. administration of STZ at 60 mg/kg, freshly dissolved in sterile sodium citrate (0.05M, pH4.5) on 6 subsequent days. Control animals received sodium citrate only. Diabetes was verified 16-25 days later by measurement of blood glucose levels in samples from the tail vein using ACCU-CHEK glucose sticks and a conventional Accutrend glucometer. In the first 2 weeks following the onset of diabetes, blood glucose was measured daily. If glucose levels occasionally recovered, an additional STZ injection was given on day 25-27. More than 90% of mice became diabetic within the first 4 weeks and were used throughout the experiment. As soon as blood glucose increased above 300 mg/dl, individual supplementation with 1-2 U Insulin Semilenta (40 U/ml) was started. Once glucose levels had stabilized, blood glucose was determined at least once a week for the first 2 months, and thereafter every second week. Tight blood glucose control kept individual blood glucose level stable throughout the experiments. At the end of the experiments, mice were sacrificed with $CO_2$, and both sciatic nerves dissected, weighed and snap-frozen in liquid nitrogen.

Isolation of DRG Cells and Ganaglian Cell Culture.

L1-L6 DRG neurons isolation and cultured was performed as described by Stucky and Lewin [39]. Briefly, DRGs were excised and roots and membranes were removed and placed in sterile calcium and magnesium-free PBS. Ganglia were collected and resuspended in DMEM/F12 (1:1, v/v) containing 10% horse serum, 2% penicillin-streptomycin Solution, 1% L-glutamine and 0.8% D-glucose (w/v). 0.1% collagenase was added and the tissue incubated at 37° C. for 45 mins. The tissue was incubated for a further 45 mins in growth medium containing 0.05% trypsin at 37° C. Individual cells were then dissociated by trituration through a fire-polished Pasteur pipette. After centrifugation at 250 g for 5 mins, the resultant pellet was washed twice in growth medium. Finally, cells were plated immediately, either onto a 6-well plate or glass coverslips which had previously been coated with poly-L-ornithine (1 μg/ml) and laminin (25 μg/ml) supplemented with murine nerve growth factor (100 ng/ml). Cells were maintained in an incubator at 37° C. with 5% $CO_2$. After 24 hrs incubation, the culture medium was supplemented with cytosine arabinoside (10 μM) and incubated for a further 12 hrs, after which time, culture medium was changed every two days until 70-80% confluence was reached.

Measurements of Hyperalgesia.

Hyperalgesia was studied using the hot-plate assay with an electronically controlled hot-plate analgesia meter (Columbus Instructments, Columbus, Ohio) at 50° C. [40,41]. Each mouse was removed from the hot plate when a jumping escape response occurred or hind paws were licked, or after a maximal cut-off time of 60 seconds. The latency until mice showed the first signs of discomfort (hind pare lifting, licking, or shaking, and jumping) was recorded by 2 investigators. Three measurements were taken per animal at each of the specified time points and averaged. The difference in latency times between control and treated animals, was calculated as a measure of hyperalgesia.

The foot withdrawal latency of the mice was also measured using the Hargreaves apparatus (Ugo, Basile, Italy) [42]. The cut-off time of the equipment was preset at 33 secs with an intensity of 60. Briefly, each mice was placed into the testing enclosure and allowed time (ca. 30 mins) to acclimatize before measurements were taken. Three measurements of foot withdrawal latency were made on each animal using alternating hind paws. Each trial was separated by an interval of 5 mins to decrease the possibly of skin injury and alteration of sensitivity of cutanous nociceptors. As for the hot-plate assay, the latency until mice showed the first signs of discomfort was recorded and the differences in latency times between control and treated animals determined.

RNA Extraction and Quantitative Real-Time PCR.

Total RNA from sciatic nerves was extracted using Trizol (Invitrogen) and from cultured DRGs using RNeasy mini kit (Qiagen, Hilden, Germany) both according to the manufacturer's instructions. A total of 2 μg of total RNA from either sciatic nerves or DRGs was annealed with 1 μg of oligo d(T) (Promega, Heidelberg, Germany) at 65° C. for 10 mins and then used for reverse transcriptase with 15 units avian myeloblastosis reverse transcriptase (Promega, Heidelberg, Germany) at 42° C. for 1 hr. cDNA was used immediately or stored at −80° C. Real time-PCR was performed on a LightCycler (Roche, Mannhiem, Germany). 4.1 cDNA, were mixed with the appropriate primers (5 μmol) and SYBR Green reagents (Roche, Mannhiem, Germany) to a final volume of 20 μl. The primers used are summarized in table 1. Cycling conditions were (95° C., 10 min); (95° C., 10 sec; 57° C., 5 sec; 72° C., 5 sec)x45; (65° C., 15 min). The expected PCR products were ca. 180 bp.

TABLE 2

Primers used for real-time PCR experiments

| | | |
|---|---|---|
| mGlyoxalase I-For | 5'- CCTCGTGGATTTGGTCACATT -3' | SEQ ID NO. 3 |
| mGlyoxalase I-Rev | 5'- GGCACATTCTCCCGAAACTAA -3' | SEQ ID NO. 4 |
| mGAPDH-For | 5'- AACGACCCCTTCATTGAC -3' | SEQ ID NO. 5 |
| mGAPDH-Rev | 5'- TCCACGACATACTCAGCAC -3' | SEQ ID NO. 6 |
| mNav1.8-For | 5'- TCGAGATGTTGCTCAAGTGG -3' | SEQ ID NO. 7 |
| mNav1.8-Rev | 5'- TACCCTCATGCCTTCGAATC -3' | SEQ ID NO. 8 |
| mNav1.9-For | 5'- AAGAGATGCAGGAGGCAAAA -3' | SEQ ID NO. 9 |
| mNav1.9-Rev | 5'- AGGCATCACATTCACCACAA -3' | SEQ ID NO. 10 |
| mTRPA1-For | 5'- AGGTGATTTTTAAAACATTGCTGAG -3' | SEQ ID NO. 11 |
| mTRPA1-Rev | 5'- CTCGATAATTGATGTCTCCTAGCAT -3' | SEQ ID NO. 12 |
| mTRPV1-For | 5'- TTCCTGCAGAAGAGCAAGAAGC -3' | SEQ ID NO. 13 |
| mTRPV1-Rev | 5'- CCCATTGTGCAGATTGAGCAT -3' | SEQ ID NO. 14 |
| mCOX2-For | 5'- GATGAGCAACTATTCCAAACCAG -3' | SEQ ID NO. 15 |
| mCOX2-Rev | 5'- CCGCTCAGGTGTTGCACGTAG -3' | SEQ ID NO. 16 |

Preparation of Total Protein Extractions.

For sciatic nerves, frozen tissue samples were grounded to a fine powder using liquid nitrogen. The homogenate was resuspended in ice-cold lysis buffer (10 mM HEPES; 10 mM KCl, 1.5 mM $MgCl_2$, 1 mM EDTA, 0.6% NP40, 0.5 mM DTT, 0.2 mM PMSF; pH7.9) and incubated on ice for 20 mins. The tissue homogenates were then vortex and centrifuged (14000 rpm; 10 mins; 4° C.), and supernatants retained for analysis.

For cultured DRGs, cells were washed twice with ice-cold 0.9% NaCl and incubated on ice for 10 mins before cells were scraped thoroughly and collected by centrifugation (2500 rpm; 10 mins; 4° C.). Cell pellet was resuspended in 0.15 ml of ice-cold lysis buffer (100 mM sodium phosphate buffer, 0.1% Triton X100, 0.5 mM DTT, 0.2 mM PMSF; pH7.4) and lysis by sonication (80%; 3×15 secs). The cell homogenates were then centrifuged (14000 rpm; 10 mins; 4° C.), and supernatants retained for analysis. The protein concentration for cell and tissue homogenates was determined by Bradford assay using BSA as a standard [43].

Assay of Glyoxalase I Activity.

Glyoxalase I activity was determined by using the spectrometric method, which monitors the initial rate of change in absorbance at 240 nm caused by the formation of S-D-lactoglutathioine [44]. For the conversion of the hemithioacetal to S-D-lactoylglutathione, the change in molar extinction coefficient $\Delta\epsilon_{240}$=2.86 $mM^{-1}$ $cm^{-1}$. The standard assay mixture contained 2 mM methylglyoxal and 2 mM GSH in sodium phosphate buffer (50 mM, pH6.6, 37° C.). The reaction mixture was allowed to stand for 10 mins before the addition of the cytosolic protein fraction (20 μg) to ensure the equilibrium of hemithioacetal formation.

Plasma Methylglyoxal Measurements.

The concentration of methylglyoxal in mouse plasma samples was determined by derivatization with 1,2-diamino-4,5-dimethoxybenezene using a previously described method [45-47]. Blood samples were drawn into EDTA containing tubes from the retrobulbar vessels at time of sacrifice and centrifuged (2000 g; 5 mins). Plasma was removed and acidified with 10% TCA (0.1 ml). Samples were either analyzed immediately or stored at −80° C.

Western Blotting.

Total protein extract from sciatic nerves or cultured DRGs (20 μg) were incubated in Laemmli loading buffer at 95° C. for 5 mins and separated under denaturing conditions on 10% Tris-glycine acrylamide gel and transferred to a nitrocelluose membrane and blocked with 5% nonfat dry milk at room temperature for 1 hr. Membranes were then incubated for a further hour with a goat polyclonal anti-Glyoxalase IgG antibody, 1:500 dilution, (Santa Cruz, Santa Cruz, USA) in 5% non-fat dry milk in PBS containing 0.05% Tween20 (PBS-T). After being washed with PBS-T, the membranes were incubated with horseradish peroxidase coupled donkey-anti-goat IgG secondary antibody, 1:1000, (Santa Cruz, Santa Cruz, USA) for 45 mins. Immunoreactive proteins were visualized on x-ray films using ECL-detection reagents according to the manufacturer's instructions and an exposure time of ca. 10 mins.

Immunohistochemistry.

Following extraction and isolation, DRGs were cultured on coverslips under hyperglycaemic conditions (30 mM glucose) for three days, and stained for Glyoxalase I. The medium was removed and the cells washed with PBS prior to fixation in 4% paraformaldehyde. The slides were treated with 3% hydrogen peroxide in methanol for 5 mins at room temperature. Blocking was performed with 3% normal horse serum for 30 mins at room temperature before the monoclonal mouse anti-glyoxalase antibody (SouthWestern Med. School, Dallas, USA) was used as primary antibody (1:150). Slides were washed three times for 2 mins with PBS and detection of signal was performed using the Vectastain ABC kit for mouse IgG (Vector Laboratories Inc., Burlingham, Calif., USA), according to the manufacturer's instructions. Peroxidase activity was visualized with 0.05% 3,3-diaminobenzisine-tetrathydrochloride (Vector Laboratories Inc.) before the slides were counterstained with Mayer's hematoxylin (Vector Laboratories Inc.). Sciatic nerve tissue was also stained for Glyoxalase I. Tissue was fixated in 4% paraformaldehyde for 15 mins at room temperature. Frozen sections (4 μm) were made and the subsequent slides treated as described above, with the exception that the primary antibody used was a polyclonal goat anti-glyoxalase antibody (Santa Cruz, Santa Cruz, USA) and detection of the signal performed using the Vectastain ABC kit for goat IgG (Vector Laboratories Inc.). Controls for immunospecificity were included in all experiments by omission of primary antibody and replacing it with PBS and matching concentrations of serum. Staining intensities were evaluated according to the following score: 0, negative staining; 1, weak staining intensity; 2, moderate staining intensity; 3, strong staining intensity.

In Vivo Methylglyoxal Treatment.

Healthy wild-type mice (Male; 10-12 weeks) were treated with various concentrations of methylglyoxal (0.7 μM-700 μM) by intravenous injection as 0.9% NaCl solution. Control groups were injected with 0.9% NaCl solution. After 3 hrs incubation time, hyperalgesia was assessed.

In Vivo Overexpression of Glyoxalase I by Somatic Gene Transfer.

Full length murine Glyoxalase I cDNA was cloned into the pCMV6-Neo expression vector under the control of a cytomegalovirus promoter. pGL3-Luciferase vector was used as a control. A concentration of 1.5 μg/g of vector or GLO1 plasmid DNA was suspended in 150 μl liposomal transfection reagent (DOTAP; Roche, Mannheim, Germany) and incubated for 15 mins at room temperature before administration by intraperitoneal injection every $4^{th}$ day in diabetic wild-type (Male; 18-20 weeks) mice for a total of 10 days. Hyperalgesia was measured before injection. At the end of the experiment, all mice were sacrificed and plasma isolated for determination of methylglyoxal concentration.

In Vivo Inhibition of Glyoxalase I.

Healthy wild-type mice (Male; 10-12 weeks) were pretreated for 48 hrs with 50 μg/g (i.p) of the cell permeable Glyoxalase I inhibitor, S-p-Bromobenzylglutathioine Cyclopentyl diester. After 48 hrs, hyperalgesia was assessed. Mice were then treated every $2^{nd}$ day for a period of 15 days, during which consecutive assessments of hyperalgesia were made. At selected time points, mice sacrificed, and plasma isolated for determination of methylglyoxal concentration.

Inhibition of Voltage-Gated Sodium Channels.

Healthy wildtype mice (12 wks; Male) were administered methylglyoxal (70 μM) by intravenous injection for 90 mins, after which time, mice were treated with either tetrodotoxin (TTX; 5-7.5 ng/g) by subcutaneous injection or with ambroxol (AMX; 500 μg/g in 1% methylcellulose) by oral administration. After an additional 90 mins, hyperalgesia was assessed. To determine the effect of ambroxol on diabetes induced pain, diabetic wildtype mice (18 wks, Male) were administered ambroxol as previously described. Hyperalgesia was measured before and after (3 hrs) administration.

In Vivo siRNA Treatments.

Pre-designed siRNA for murine voltaged-gated sodium channels 1.8, 1.9 (Scn10a and Scn11a, respectively), TRPA1 and TRPV1 and were purchased from Ambion® (Applied Biosystems). A concentration of 1.5 μg/g of siRNA were suspended in 150 μl liposomal transfection reagent (DOTAP; Roche, Mannheim, Germany) and incubated for 15 mins at room temperature before administration by intravenous injection every $3^{rd}$ day for a period of 10 days in healthy wildtype mice (Male; 10-12 weeks). On the tenth day, mice were injected with either methylglyoxal (70 μM) or PBS as a control. After 3 hrs, hyperalgesia was assessed and the mice sacrificed. To confirm knock-down of treated mice, sciatic nerves and DRGs were removed and total RNA was extracted and real-time PCR performed, as described.

In Vivo Scavanging of Methylglyoxal.

A synthetic peptide, GERP001, containing ten arginine residues per molecule act as an effective in vivo scavenger of methylglyoxal was designed in house and synthesized (GenWay Biotech, Inc. San Diego, Calif., USA). Healthy wild-type mice (Male; 10-12 weeks) were injected intraperitioneal with 1 mg of either the GERP001 or GEAP, a control peptide in which the arginine residues were substituted for alanine, 30 mins prior to injection with either 0.9% NaCl (Control) or methylglyoxal (70 μM). Hyperalgesia was assessed 3 hrs after administration of methylglyoxal.

To determine the effect of GERP on diabetes induced hyperalgesia, STZ-induced diabetic wild-type mice (Male; 18 wks) were injected intraperitioneal with either 1 mg of GERP001 or GEAP. After 24 hrs, hyperalgesia was assessed by hotplate assay.

Immunoprecipitation (IP) and Western Blot Analysis.

PC12 cells were plated into 175 $cm^2$ culture dishes and grown in RPMI 1640 medium supplemented with 10% horse serum, 5% fetal bovine serum and 1% streptomycin/penicillin solution. Cells were kept in culture at 37° C., in a $CO_2$ incubator. Once cells had reached a state of confluencey (ca. $20\times10^6$), cells were treated with 30 mM D-glucose or methylglyoxal (50-500 μM) for 3 hrs or Glyoxalase I inhibitor (4 μM) for 24-72 hrs.

Healthy wild-type Sprague-Dawley rats (12 wks; Male) were treated with methylglyoxal (70 μM) by intravenous injection as 0.9% NaCl solution. Control groups were injected with 0.9% NaCl solution. After 3 hrs, the rats were sacrificed with $CO_2$ and the L4-L5 lumber DRGs were removed and either processed immediately or snap frozen in liquid nitrogen or kept at −80° C.

Both tissue and cell samples were homogenized in a glass dounce ice-cold lysis buffer (0.3M sucrose, 10 mM Tris, 2 mM EDTA; pH8.1) at 30 μl/mg cell. Homogenates were kept on ice for 1 h before centrifugation (2500 rpm for 7 mins at 4° C.) to remove nuclei and intact cells. The pellet was then re-homogenized and spun again under the same conditions. The supernatants from the two low-speed spins were combined and centrifuged at 45,000 rpm for 2 hrs at 4° C. The pellet, containing the total membrane fraction, was re-suspended in 0.2M KCl and 10 mM HEPES (pH7.4). Membranes were then solubilised by addition of an equal volume of 5% Triton X100 and 10 mM HEPES (pH7.4) and the suspension kept on ice for 1 hr. Unsolublized material was pelleted by centrifugation at 12000 rpm for 10 mins at 4° C. and the soluble material retained and protein concentration determined by Bradford assay [43].

Crude membrane fractions (500 μs) were precleared by normal serum plus Protein A/G-agarose beads (Santa Cruz, Santa Cruz, USA) for 1 hr and the supernatants immunoprecipiated with 5 μg of antibodies for either Nav1.8 (Sigma, St. Louis, Mo., USA), TRPA1 or TRPVA (Santa Cruz, Santa Cruz, USA) overnight at 4° C. with gentle agitation. Protein A/G-agarose beads (Santa Cruz, Santa Cruz, USA) were added and incubated for a further 6 hrs. Beads were collected by centrifugation (10,000 g for 10 mins at 4° C.) and washed three time with buffer containing 20 mM Tris (pH7.5), 150 mM NaCl, 5 mM EDTA, 0.2% SDS, 1% Triton X-100, 0.1 mM PMSF, 1 U/ml aprotinin. Protein were released from the agarose beads by incubation in denaturing buffer (125 mM Tris-HCl, 4% SDS, 20% Glycerol, 10% 13-Mercaptoethanol; pH6.8; 50 μl) at 95° C. for 10 mins. The beads were collected by centrifugation, and the resulting supernatants retained and stored at −80° C. for further analysis.

The immunioprecipated were analyzed either by dot blot or western blot analysis. For the dot blot analysis, 2 μl of the immunoprecipitate were blotted onto a nitrocelluose membrane and blocked with 5% nonfat dry milk at room temperature for 1 hr. Membranes were then incubated for 45 mins at room temperature with antibodies for either methylglyoxal derived AGEs (BioLogo, Kronshagen, Germany), Nav1.8, TRPA1 or TRPV1 (1:500) in 5% non-fat dry milk in PBS containing 0.05% Tween20 (PBS-T). After being washed with PBS-T, the membranes were incubated with appropriate horseradish peroxidase coupled secondary antibody for 1 hr at room temperature (1:1000; Santa Cruz, Santa Cruz, USA). Immunoreactive proteins were visualized on x-ray films using ECL-detection reagents according to the manufacturer's instructions and an exposure time of ca. 5 mins. For western blot analysis, immunoprecipiates were separated on a 4-12% SDS-PAGE gel and transferred to a nitrocelluose membrane. Visualization of the methylglyoxal modified proteins was achieved using the One-Step™ Complete IP-Western Kit (GeneScript Corp, NJ, USA) according to the manufacturer's instructions using an antibody for methylglyoxal derived AGEs (BioLogo, Kronshagen, Germany; 10 μg). Immunoreactive proteins were visualized on x-ray films using ECL-detection reagents according to the manufacturer's instructions and an exposure time of ca. 10 mins.

Molecular Modelling.

Receptor binding domain (RBD) analysis to determine likely sites of methylglyoxal modification in Nav1.8 from human, rat and mouse. Briefly, the amino acid sequence for Nav1.8 (Accession No. Q9Y5Y9, Human; Accession No. Q62968, Rat; Accession No. Q6QIY3, Mouse) were obtained from the UniProtKB/Swiss-Prot database. Residue hydrophobicity was calculated using Protscale, and mean hydrophobic moment calculated using Embosswin. Both hydrophobicity and the mean hydrophobic moment values were aligned with the sequence number to generate a plot of hydrophobicity vs. mean hydrophobic moment, sectioned as described by Gallet et al [48]. Arginine and lysine residues found within the RBD were then highlighted as potential hotspots for modification by methylglyoxal. Attempts to identify those arginine and lysine residues with a higher potential for modification based upon differences in residue pKa were not possible as no complete crystal structure is available for Nav1.8. Instead, identification was made, with reference to the amino acid sequence, based upon the following criteria that arginine and lysine residues most reactive with methylglyoxal are those with proximate arginine and lysine residues that decrease the pKa of both interacting amino groups and have glutamic or aspartic acid carboxylate side chain on the alternate side in the sequence to act as a catalytic base [48,50]. Using this selection criterion, the total number of glycation hotspots was established. Multiple sequence alignment was performed using Bioedit with in built ClustW.

Statistics

Significant difference between mean latency times for control and treated was determined using Student's t-test and was performed using the statistical package in Microsoft Excel.

The features disclosed in the foregoing description, in the claims and/or in the accompanying drawings may, both separately and in any combination thereof, be material for realizing the invention in diverse forms thereof.

REFERENCES

1. Castegna, A. et al., (2002) Proteomic identification of oxidatively modified proteins in Alzheimer's disease brain Part I: creatine kinase BB, glutamine synthase, and ubiquitin carboxyl-terminal hydrolase L-1. *Free Radic. Biol. Med.* 33.562-571.

2. Butterfield, D. A., and Lauderback, C. M. (2002) Lipid peroxidation and protein oxidation in Alzheimer's disease brain: potential causes and consequences involving amyloid 13-peptide-associated free radical oxidative stress. *Free. Radic. Biol. Med.* 32, 1050-1060.
3. Hensley, K. et al., (1995) Brain regional correspondence between Alzheimer's disease histopathology and biomarkers of protein oxidation. *J. Neurochem.* 65, 2146-2156.
4. Aksenov, M. Y. et al., (2001) Protein oxidation in the brain in Alzheimer's disease. *Neuroscience.* 103, 373-383
5. Aksenov, M. Y. et al., (2000) Oxidative modification of creatine kinase BB in Alzheimer's disease. *J. Neurochem.* 74, 2520-2527
6. Castegna, A. et al., (2000) Proteomic identification of oxidatively modified proteins in Alzheimer's disease brain Part II: dihydropyrimidinase-related protein 2, α-enolase and heat shock cognate 71. *J. Neurochem.* 82, 1524-1532.
7. Conrad, C. C., et al., (2000) Oxidized proteins in Alzheimer's plasma. *Biochem. Biophys. Res. Commun.* 275, 678-681.
8. Choi, J., et al., (2002) Identification of oxidized plasma proteins in Alzheimer's disease. *Biochem. Biophys. Res. Commun.* 293, 1566-1570.
9. Chen, K., et al., (2007) Effect of aldehydes derived from oxidative deamination and oxidative stress on β-amyloid aggregation: pathological implications to Alzheimer's disease. *J. Neural Trans.* 114, 835-839.
10. Ahmed, N., et al., (2005) Protein glycation, oxidation and nitration adduct residues and free adducts of cerebrospinal fluid in Alzheimer's disease and link to cognitive impairment. *J. Neurochem.* 92, 255-263.
11. Munch, G. et al., (2003) Anti-AGEing defences against Alzheimer's disease. *Biochem Soc Trans.* 31, 1397-1399.
12. Ferrante, R. J. et al (1997) Evidence of increased oxidative damage in both sporadic and familial amyotrophic lateral sclerosis. *J. Neurochem.* 69, 2064-2074.
13. Shinpo, K. et al., (2000) Selective vulnerability of spinal motor neurons to reactive dicarbonyl compounds, intermediate products of glycation, in vitro: implication of inefficient glutathione system in spinal motor neurons. *Brain Res.* 861, 151-159.
14. Boscia, F. et al. (2000) Protein oxidation and lens opacity in humans. *Invest. Ophthalmol Vis. Sci.* 41, 2461-2465
15. Shamsi, F. A., et al., (1998) Methylglyoxal-derived modifications in lens agining and cataract formation. *Invest Ophthalmol V is Sci.* 39, 2355-2364.
16. Shami, F. A., et al., (1999) Immunodetection of dicarbonyl-derived imidazolium protein crosslinks in human lenses. *Curr Eye Res.* 19, 276-284.
17. Himmelfarb, J. et al., (2000) Plasma protein thiol oxidation and carbonyl formation in chronic renal failure. *Kidney Int.* 58, 2571-2578
18. Himmelfarb, J. and McMongle, E. (2001) Albumin is the major plasma protein target for oxidant stress in uremia. *Kidney Int* 60, 358-363
19. Lim, P. S. et al., (2002) Increase in oxidative damage to lipids and proteins in skeletal muscle of uremic patients. *Free Radic. Res.* 36, 295-301
20. Miyata, T. et al., (1999) Alterations in nonenzymatic biochemistry in uremia: origin and significance of carbonyl stress in long-term uremic complications. *Kidney Int* 55, 389-399.
21. Nakayama K, et al., (2008) Plasma alpha-oxoaldehyde levels in diabetic and non-diabetic chronic kidney disease patients. *Am J Nephrol.* 28, 871-878
22. Müller-Krebs S, et al., (2008) Renal toxicity mediated by glucose degradation products in a rat model of advanced renal failure. *Eur J Clin Invest.* 38, 296-305.
23. Rabbani N (2007) Accumulation of free adduct glycation, oxidation, and nitration products follows acute loss of renal function. *Kidney Int* 72, 1113-1121.
24. Lapolla A, et al., (2005) Evaluation of glyoxal and methylglyoxal levels in uremic patients under peritoneal dialysis. *Ann N Y Acad. Sci.* 1043, 217-224
25. Agalous, S et al., (2003) Removal of advanced glycation endproducts in clinical renal failure by peritoneal dialysis and haemodialysis. *Biochem Soc Trans.* 31, 1394-1396.
26. McGrath, L. T. et al., (1999) Oxidative stress during acute respiratory exacerbations in cystic fibrosis. *Thorax* 54, 518-523.
27. Range, S. P. et al., (1999) Treatment of pulmonary exacerbations of cystic fibrosis leads to improved antioxidant status. *Euro. Respir. J.* 13, 560-564
28. Lyras, L et al., (1998) Oxidative damage to proteins, lipids, and DNA in cortical brain regions from patients with dementia with Lewy bodies. *J. Neurochem.* 71, 302-312.
29. Pantke, U., et al., (1999) Oxidized proteins as a marker of oxidative stress during coronary heart surgery. *Free Radic. Bio. Med.* 27, 1080-1086
30. Zusterzeel, P. L. (2001) Protein carbonyls in decidua and placenta of pre-eclamptic women as markers for oxidative stress. *Placenta* 22, 213-219
31. Dimon-Gadal, S. et al., (2001) Increased oxidative damage to fibroblasts in skin with and without lesions in psoriasis. *J. Invest. Dermatol.* 114, 984-989
32. Mantle, D et al., (1999) Quantification of protease activities in synovial fluid from rheumatoid and osteoarthritis cases: comparison with antioxidant and free radical damage markers. *Clin. Chim. Acta* 284, 45-58.
33. Renke, J. et al., (2000) Protein carbonyl groups content as a useful clinical marker of antioxidant barrier impairment in plasma of children with juvenile chronic arthritis. Free *Radic. Biol. Med.* 29, 101-104.
34. Winterbourn, C. C. et al., (2000) Protein carbonyl measurements show evidence of early oxidative stress in critically ill patients. *Crit. Care. Med.* 28, 143-149
35. Abu-Zidan, F. M. et al., (2002) Proteolysis in severe sepsis is related to oxidation of plasma protein. *Eur. J. Surg.* 168, 119-123
36. Miyata, T. et al., (2000) Carbonyl stress and dialysis-related amyloidosis. *Nephrol. Dial. Transplant.* 15, 25-28.
37. Floor, E., and Wetzel, M. G. (1998) Increased protein oxidation in human substantia nigra pars compacta in comparison with basal ganglia and prefrontal cortex measured with an improved dinitrophenolhydrazine assay. *J. Neurochem.* 70, 268-275.
38. Han Y, Randell E, Vasdev S, Gill V, Curran M, Newhook L A, Grant M, Hagerty D, Schneider C: Plasma advanced glycation endproduct, methylglyoxal-derived hydroimidazolone is elevated in young, complication-free patients with Type 1 diabetes. *Clin Biochem.* 2009 Jan. 3. [Epub ahead of print]
39. Stucky, C L, Lewin, G L. Isolectin B 4-positive and -negative nociceptors are functionally distinct. *J. Neurosci.* 1999. 19:6497-6505.
40. Menendez, L, Lastra, A, Hidaldo, A, Baamonde, A. Unilateral hot plate test: a simple and sensitive method for detecting central and peripheral hyperalgesia in mice. *J. Neurosci. Methods.* 2002. 113:91-97.

41. Chen, C C, et al. A role for ASIC3 in the modulation of high intensity pain stimuli. *Proc. Natl. Acad. Sci. U.S.A.* 2002. 13:8992-8997.
42. Hargreavesm K., et al. A new and sensitive method for measuring thermal nociception in cutaneous hyperalgesia. *Pain.* 1988. 32: 77-88.
43. Bradford, M. M., A rapid and sensitive method for the quantitation of microgram quantities of protein utilizing the principle of protein-dye binding. *Anal Biochem.* 1976. 72: 248-254.
44. McLellan, A. C., Thornalley, P. J. Glyoxalase activity in human red blood cells fractionated by age. *Mech. Ageing Dev.* 1989. 48:63-71.
45. McLellan, A. C., Thornalley, P. J. Synthesis and chromatography of 1,2-diamino-4,5-dimethoxybenzene, 6,7-dimethyl-2-methylquinoxaline and 6,7-dimethylquinoxaline for use in a liquid chromatographic fluorometic assay of methylglyoxal. *Analytica Chimica Acta.* 1992. 263:137-142.
46. McLellan, A. C., Phillips, S. A., Thornalley, P. J. The assay of methylglyoxal in biological systems by derivatization with 1,2-Diamino-4,5-dimethoxybenzene. Analytical Biochemistry. 1992. 206:17-23.
47. Thornalley, P. J., Langborg, A., Minhas, H. S., Formation of glyoxal, methylglyoxal and 3-deoxyglucosone in the glycation of proteins by glucose. Biochem J. 1999. 344: 109-116.
48. Gallet et al. (2000) A fast method to predict protein interaction sites from sequences. Journal of Molecular Biology, 302(4):917-926.
49. Ahmed, N., et al. (2005). Peptide mapping identifies hotspot site of modification in human serum albumin by methylglyoxal involved in ligand binding and esterase activity. J. Biol. Chem. 280, 5724-5732.
50. Venkatraman, J., et al. (2001). Helical peptide models for protein glycation: proximity effects in catalysis of the Amadori rearrangement. Chem. Biol. 8, 611-625.
51. B. W. Erickson and R. B. Merrifield, 1976.

The invention claimed is:

1. A compound that inhibits the binding of methylglyoxal (MG) and/or reactive carbonyl species (RCS) to an arginine- or lysine-containing protein and that is a peptide comprising the GEXP motif

[Gly-Glu-X-Pro (SEQ ID NO: 1)]$_n$ wherein X is Arg or Lys and n is at least 2.

2. The peptide of claim 1, wherein n is in the range from 2≤n≤100.

3. The peptide according to claim 1, wherein the peptide forms a left-handed helix.

4. The peptide according to claim 1, having a length of 8 to 500 amino acids.

5. The compound according to claim 1, wherein the compound comprises one or more tags, labels, linkers and/or drugs.

6. The peptide according to claim 1, represented by the following formula:

N'-[Tag]$_m$-Linker-[Gly-Glu-X-Pro (SEQ ID NO: 1)]$_n$-C' wherein
X is Arg or Lys
m is at least 1,
n is at least 2,
N' denotes the N-terminus, and
C' denotes the C-terminus.

7. The peptide according to claim 6, comprising
a His tag, with m=1,
a polyglycine linker, and
a GEXP motif with X=Arg and n=10.

8. The compound according to claim 1, further comprising acetylation and/or amidation of the N- and/or C-terminus.

9. The peptide according to claim 1, wherein the peptide further comprises modified amino acid(s), unnatural amino acid(s) and/or peptidomimetic(s).

10. A method for scavenging methylglyoxal (MG) and/or reactive carbonyl species (RCS) wherein said method comprises contacting MG and/or RCS with a compound of claim 1.

11. A method for inhibiting the binding of methylglyoxal to an arginine-containing protein wherein said method comprises contacting a compound of claim 1 with an arginine-containing protein in the presence of methylglyoxyal.

12. A method for the prevention and/or treatment of pain and/or hyperalgesia associated with methylglyoxal and/or reactive carbonyl species (RCS) wherein said method comprises administering, to a subject in need of such treatment and/or prevention, a compound of claim 1.

13. The method according to claim 12, wherein the pain and/or hyperalgesia to be prevented and/or treated is associated with and/or occurs during a disease, wherein said disease is selected from Alzheimers disease, amyotrophic lateral sclerosis, cataractogenesis, chronic renal failure and chronic or acute Uraemia, cystic fibrosis, dementia with Lewy bodies, diabetes mellitus and its complications, ischaemia-reperfusion, pre-eclampsia, psoriasis, rheumatoid arthritis and juvenile chronic arthritis, severe sepsis, systemic amyloidosis, Parkinson's disease, painful bowel disease, chemotherapy induced pain, critical limb ischemia, hypertension, bone pain, and tumor pain.

14. A pharmaceutical composition comprising at least one compound according to claim 1, and, optionally, a pharmaceutically acceptable carrier and/or excipient.

15. A method for identifying a compound that influences pain and/or hyperalgesia caused by or associated with methylglyoxal and/or reactive carbonyl species (RCS), comprising (a) providing a compound to be screened, (b) providing a compound according to claim 1, (c) providing methylglyoxal and/or RCS to both compounds of (a) and (b); and (d) assessing, following step (c), whether the compound of (a) binds to methylglyoxal and/or RCS to determine if the compound of (a) influences pain and/or hyperalgesia.

16. The peptide, according to claim 7, comprising the amino acid sequence of SEQ ID NO 2.

17. The method, according to claim 11, wherein the protein is a cellular sodium ion channel protein.

18. The method, according to claim 13, wherein the pain to be prevented and/or treated is allodynia.

* * * * *

SEQUENCE LISTING

```
<160> NUMBER OF SEQ ID NOS: 19

<210> SEQ ID NO 1
<211> LENGTH: 4
<212> TYPE: PRT
<213> ORGANISM: Artificial
<220> FEATURE:
<223> OTHER INFORMATION: GEXP motif, wherein X is Arg or Lys
<220> FEATURE:
<221> NAME/KEY: misc_feature
<222> LOCATION: (3)..(3)
<223> OTHER INFORMATION: Xaa is a basic amino acid Arg or Lys

<400> SEQUENCE: 1

Gly Glu Xaa Pro
1


<210> SEQ ID NO 2
<211> LENGTH: 50
<212> TYPE: PRT
<213> ORGANISM: Artificial
<220> FEATURE:
<223> OTHER INFORMATION: GEXP motif containing peptide

<400> SEQUENCE: 2

His His His His His His Gly Gly Gly Gly Gly Glu Arg Pro Gly Glu
1               5                   10                  15

Arg Pro Gly Glu Arg Pro Gly Glu Arg Pro Gly Glu Arg Pro Gly Glu
            20                  25                  30

Arg Pro Gly Glu Arg Pro Gly Glu Arg Pro Gly Glu Arg Pro Gly Glu
        35                  40                  45

Arg Pro
    50


<210> SEQ ID NO 3
<211> LENGTH: 21
<212> TYPE: DNA
<213> ORGANISM: Artificial
<220> FEATURE:
<223> OTHER INFORMATION: Primer mGlyoxalase I - For

<400> SEQUENCE: 3

cctcgtggat ttggtcacat t                                                 21
```

-continued

<210> SEQ ID NO 4
<211> LENGTH: 21
<212> TYPE: DNA
<213> ORGANISM: Artificial
<220> FEATURE:
<223> OTHER INFORMATION: Primer mGlyoxalase I - Rev

<400> SEQUENCE: 4
ggcacattct cccgaaacta a 21

<210> SEQ ID NO 5
<211> LENGTH: 18
<212> TYPE: DNA
<213> ORGANISM: Artificial
<220> FEATURE:
<223> OTHER INFORMATION: Primer mGAPDH - For

<400> SEQUENCE: 5
aacgacccct tcattgac 18

<210> SEQ ID NO 6
<211> LENGTH: 19
<212> TYPE: DNA
<213> ORGANISM: Artificial
<220> FEATURE:
<223> OTHER INFORMATION: Primer mGAPDH - Rev

<400> SEQUENCE: 6
tccacgacat actcagcac 19

<210> SEQ ID NO 7
<211> LENGTH: 20
<212> TYPE: DNA
<213> ORGANISM: Artificial
<220> FEATURE:
<223> OTHER INFORMATION: Primer mNav1.8 - For

<400> SEQUENCE: 7
tcgagatgtt gctcaagtgg 20

<210> SEQ ID NO 8
<211> LENGTH: 20
<212> TYPE: DNA
<213> ORGANISM: Artificial
<220> FEATURE:
<223> OTHER INFORMATION: Primer mNav1.8 - Rev

<400> SEQUENCE: 8
taccctcatg ccttcgaatc 20

<210> SEQ ID NO 9
<211> LENGTH: 20
<212> TYPE: DNA
<213> ORGANISM: Artificial
<220> FEATURE:
<223> OTHER INFORMATION: Primer mNav1.9 - For

<400> SEQUENCE: 9
aagagatgca ggaggcaaaa 20

<210> SEQ ID NO 10
<211> LENGTH: 20
<212> TYPE: DNA
<213> ORGANISM: Artificial
<220> FEATURE:
<223> OTHER INFORMATION: Primer mNav1.9 - Rev -continued

<400> SEQUENCE: 10
aggcatcaca ttcaccacaa 20

<210> SEQ ID NO 11
<211> LENGTH: 25
<212> TYPE: DNA
<213> ORGANISM: Artificial
<220> FEATURE:
<223> OTHER INFORMATION: Primer mTRPA1 - For

<400> SEQUENCE: 11
aggtgatttt taaaacattg ctgag 25

<210> SEQ ID NO 12
<211> LENGTH: 25
<212> TYPE: DNA
<213> ORGANISM: Artificial
<220> FEATURE:
<223> OTHER INFORMATION: Primer mTRPA1 - Rev

<400> SEQUENCE: 12
ctcgataatt gatgtctcct agcat 25

<210> SEQ ID NO 13
<211> LENGTH: 22
<212> TYPE: DNA
<213> ORGANISM: Artificial
<220> FEATURE:
<223> OTHER INFORMATION: Primer mTRPV1 - For

<400> SEQUENCE: 13
ttcctgcaga agagcaagaa gc 22

<210> SEQ ID NO 14
<211> LENGTH: 21
<212> TYPE: DNA
<213> ORGANISM: Artificial
<220> FEATURE:
<223> OTHER INFORMATION: Primer mTRPV1 - Rev

<400> SEQUENCE: 14
cccattgtgc agattgagca t 21

<210> SEQ ID NO 15
<211> LENGTH: 23
<212> TYPE: DNA
<213> ORGANISM: Artificial
<220> FEATURE:
<223> OTHER INFORMATION: Primer mCOX2 - For

<400> SEQUENCE: 15
gatgagcaac tattccaaac cag 23

<210> SEQ ID NO 16
<211> LENGTH: 21
<212> TYPE: DNA
<213> ORGANISM: Artificial
<220> FEATURE:
<223> OTHER INFORMATION: Primer mCOX2 - Rev

<400> SEQUENCE: 16
ccgctcaggt gttgcacgta g 21

<210> SEQ ID NO 17
<211> LENGTH: 7
<212> TYPE: PRT

-continued

```
<213> ORGANISM: Artificial
<220> FEATURE:
<223> OTHER INFORMATION: histidine tag

<400> SEQUENCE: 17

His His His His His His His
1               5


<210> SEQ ID NO 18
<211> LENGTH: 4
<212> TYPE: PRT
<213> ORGANISM: Artificial
<220> FEATURE:
<223> OTHER INFORMATION: glycine linker

<400> SEQUENCE: 18

Gly Gly Gly Gly
1


<210> SEQ ID NO 19
<211> LENGTH: 40
<212> TYPE: PRT
<213> ORGANISM: Artificial
<220> FEATURE:
<223> OTHER INFORMATION: GEAP motif containing peptide

<400> SEQUENCE: 19

His His His His His His Gly Gly Gly Gly Gly Glu Pro Gly Glu Pro
1               5                   10                  15

Gly Glu Pro Gly Glu Pro Gly Glu Pro Gly Glu Pro Gly Glu Pro Gly
            20                  25                  30

Glu Pro Gly Glu Pro Gly Glu Pro
        35                  40
```